(12) United States Patent
Alonso-Bedate et al.

(10) Patent No.: US 10,000,538 B2
(45) Date of Patent: Jun. 19, 2018

(54) MOLECULE FOR TREATING AN INFLAMMATORY DISORDER

(75) Inventors: Carlos Alonso-Bedate, Madrid (ES); Manuel Soto-Alvarez, Madrid (ES); Laura Ramirez-Garcia, Madrid (ES); Jeronimo Carnés-Sánchez, Madrid (ES); Marta Román-Escutia, Madrid (ES)

(73) Assignee: LABORATORIOS LETI, S.L., Madrid (ES)

( * ) Notice: Subject to any disclaimer, the term of this patent is extended or adjusted under 35 U.S.C. 154(b) by 0 days. days.

(21) Appl. No.: 14/116,301

(22) PCT Filed: May 8, 2012

(86) PCT No.: PCT/EP2012/058453
§ 371 (c)(1),
(2), (4) Date: Apr. 10, 2014

(87) PCT Pub. No.: WO2012/152792
PCT Pub. Date: Nov. 15, 2012

(65) Prior Publication Data
US 2014/0206598 A1   Jul. 24, 2014

Related U.S. Application Data
(60) Provisional application No. 61/484,167, filed on May 9, 2011.

(30) Foreign Application Priority Data
May 9, 2011 (EP) .................................. 11165248

(51) Int. Cl.
*A61K 38/00* (2006.01)
*C07K 14/44* (2006.01)
*A61K 39/008* (2006.01)
*A61K 39/39* (2006.01)
*A61K 39/00* (2006.01)

(52) U.S. Cl.
CPC ............ *C07K 14/44* (2013.01); *A61K 39/008* (2013.01); *A61K 39/39* (2013.01); *A61K 2039/55516* (2013.01); *C07K 2319/21* (2013.01); *C07K 2319/24* (2013.01)

(58) Field of Classification Search
None
See application file for complete search history.

(56) References Cited

U.S. PATENT DOCUMENTS 6,054,135 A * 4/2000 Reed ............... C07K 14/44
424/185.1
2005/0079186 A1   4/2005 Papierok et al.
2012/0263746 A1* 10/2012 Alonso-Bedate ...... C07K 14/44
424/191.1

FOREIGN PATENT DOCUMENTS

WO   2011-0580137 A1   5/2011

OTHER PUBLICATIONS

Ivens et al. The genome of the kinetoplastid parasite, Leishmania major. Jul. 15, 2005. Science. vol. 309, No. 5733, pp. 436-442.*
Sequence Alignment for SEQ ID No. 1. Conducted on Mar. 18, 2015, 2 pages.*
Sequence Alignment for SEQ ID No. 1 with SEQ ID No. 52 of U.S. Pat. No. 6,054,135. Conducted on Sep. 24, 2015, 2 pages.*
International Search Report of PCT/EP2012/058453 dated Jul. 9, 2012, 4 pages.
Database UniProt (Online), "Putative 60S Ribosomal Protein L19," retrieved from EBI Accession No. UNIPROT: Q4QJ39 sequence (Jul. 19, 2005), 1 page.
Iborra., S., et al., "Vaccination with the Leishmania Major Ribosomal Proteins Plus CpG Oligodeoxynucleotides Induces Protection Against Experimental Cutaneous Leishmaniasis in Mice," Microbes and Infection, vol. 10, No. 10-11, pp. 1133-1141 (Aug. 1, 2008).
Kuroda, K., et al., "Identification of Ribosomal Protein L19 as a Novel Tumor Antigen Recognized by Autologous Cytotoxic T Lymphocytes in Lung Adenocarcinoma," Cancer Science, vol. 101, No. 1, pp. 46-53 (Jan. 1, 2010).
Rodrigues, I., et al., Review Article "Natural Products: Insights into Leishmaniasis Inflammatory Response," Mediators of Inflammation, vol. 2015, Article ID 835910, pp. 1-12 (Jul. 22, 2015).
Zhou, X., et al., "Boosting Interleukin-10 Production: Therapeutic Effects and Mechanisms," Current Drug Targets—Immune, Endocrine & Metabolic Disorders, vol. 5, No. 4, pp. 465-475 (Dec. 2005).
Genbank Accession No. XM 001463085—Peacock, C.S., et al., Apr. 27, 2007, 2 pages.
Genbank Accession No. XM 001680759—Ivens, A.C., et al., Oct. 4, 2007, 2 pages.
Genbank Accession No. XM 001561924—Peacock, C.S., et al., Jul. 31, 2007, 2 pages.
Genbank Accession No. XM 001463087—Peacock, C.S., et al., Apr. 27, 2007, 2 pages.
Genbank Accession No. XM 001561926—Peacock, C.S., et al., Jul. 31, 2007, 2 pages.
Genbank Accession No. XM 001680811—Ivens, A.C., et al., Oct. 4, 2007, 2 pages.
Genbank Accession No. XP 001463122—Peacock, C.S., et al., Apr. 27, 2007, 2 pages.
Genbank Accession No. XP 001463124—Peacock, C.S., et al., Apr. 27, 2007, 2 pages.
Genbank Accession No. XP 001561976—Peacock, C.S., et al., Jul. 31, 2007, 2 pages.
Genbank Accession No. XP 001561974—Peacock, C.S., et al., Jul. 31, 2007, 2 pages.
Asadullah, K., et al., "Cytokine Therapy in Dermatology," Experimental Dermatology, vol. 11, Issue 2, pp. 97-106 (Apr. 2002).
Bee, A., et al., "Ribosomal Protein L19 is a Prognostic Marker for Human Prostate Cancer", Clin. Cancer Res., 12(7) Apr. 1, 2006.

(Continued)

*Primary Examiner* — Channing S Mahatan
(74) *Attorney, Agent, or Firm* — Polsinelli PC; Christopher M. Cabral

(57) ABSTRACT

The invention provides a L19 source as a medicament, preferably for preventing or treating an inflammatory disorder in an individual.

12 Claims, 7 Drawing Sheets

(56) References Cited

OTHER PUBLICATIONS

Henry, J. L., et al., "High-Level Expression of Ribosomal Protein L19 in Human Breast Tumors That Overexpresses erbB-2," Cancer Research 53, 1403-1408, Mar. 15, 1993.
Huang, D. J., et al., "Faecal ribosomal protein L19 is a genetic prognostic factor for survival in colorectal cancer," J. Cell. Mol. Med., vol. 12, No. I 5B, 2008, pp. 1936-1943.

* cited by examiner

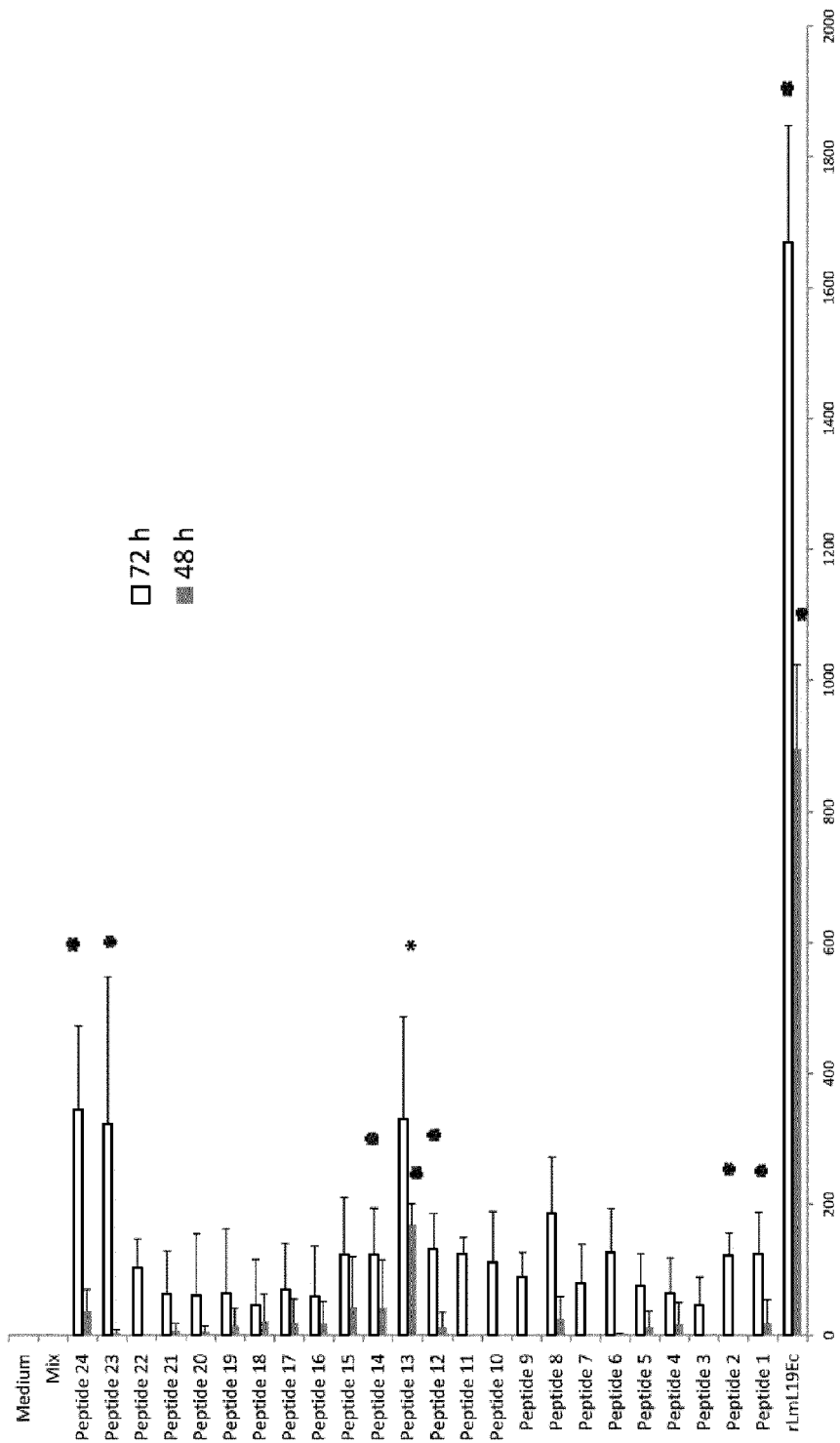

```
SEQUENCE LISTING

<160> NUMBER OF SEQ ID NOS: 57

<210> SEQ ID NO 1
<211> LENGTH: 267
<212> TYPE: PRT
<213> ORGANISM: Leishmania major

<400> SEQUENCE: 1

Met Thr Pro Leu Ser Leu Ser Ser Ser Arg His Ser Phe Lys Gln Asn
1               5                   10                  15

Glu Thr Gln Asn Met Val Ser Leu Lys Leu Gln Ala Arg Leu Ala Ser
            20                  25                  30

Ser Ile Leu Gly Cys Gly Arg Ala Arg Val Trp Leu Asp Pro Asn Glu
        35                  40                  45

Ala Val Glu Ile Gln Asn Ala Asn Ser Arg Lys Ser Val Arg Lys Leu
    50                  55                  60

Ile Lys Asp Gly Phe Ile Ile Arg Lys Pro Val Lys Val His Ser Arg
65                  70                  75                  80

Ala Arg Trp Arg Lys Met Lys Glu Ala Lys Asp Met Gly Arg His Asn
                85                  90                  95
```

```
Gly Val Gly Arg Arg Glu Gly Ser Arg Glu Ala Arg Met Pro Ser Lys
                100                 105                 110

Glu Leu Trp Met Arg Arg Leu Arg Ile Leu Arg Arg Leu Leu Arg Lys
            115                 120                 125

Tyr Arg Ala Asp Lys Lys Ile Asp Arg His Val Tyr Arg Asp Leu Tyr
        130                 135                 140

Met Arg Ala Lys Gly Asn Val Phe Arg Asn Lys Arg Asn Leu Val Glu
145                 150                 155                 160

His Ile His Lys Ile Lys Asn Glu Lys Lys Lys Glu Arg Gln Leu Ala
                165                 170                 175

Glu Gln Leu Ala Ala Lys His Leu Arg Asp Glu Gln Asn Arg Asn Lys
            180                 185                 190

Ala Arg Lys Gln Glu Leu Lys Lys Arg Glu Lys Glu Arg Glu Arg Ala
        195                 200                 205

Arg Arg Asp Asp Ala Ala Ala Ala Gln Lys Lys Ala Asp Ala
    210                 215                 220

Ala Lys Lys Ser Ala Ala Pro Ala Ala Lys Ser Ala Ala Pro Ala Ala
225                 230                 235                 240

Lys Ala Ala Ala Pro Ala Thr Lys Ala Ala Ala Ala Pro Ala Thr
                245                 250                 255

Lys Gly Ala Ala Pro Val Lys Lys Ser Lys Lys
        260                 265

<210> SEQ ID NO 2
<211> LENGTH: 804
<212> TYPE: DNA
<213> ORGANISM: Leishmania major

<400> SEQUENCE: 2
atgacccctc tctccctctc ttcctcccgc cacagtttta agcagaacga aacgcagaac    60
atggtgtctc tgaagctgca ggctcgcctt gcgtcgagca tcctcggctg cggccgcgcc   120
cgcgtgtggc tggaccccaa cgaggcggtg gagatccaga acgcgaactc gcgcaagagc   180
gtgcgcaagc tgatcaagga tggcttcatc atccgcaagc cggtgaaggt gcactcgcgc   240
gcgcggtggc gtaaaatgaa ggaggcgaag gacatggggc gccacaacgg cgttgggcgc   300
cgcgagggta gccgcgaggc ccgcatgccg agcaaggagt tgtggatgcg ccgcctgcgc   360
attctgcgcc gcctgctgcg caagtaccgc gcggacaaga agattgaccg ccacgtgtac   420
cgcgacctgt acatgcgcgc gaagggtaac gtgttccgca acaagcgcaa ccttgtggag   480
cacatccaca agatcaagaa tgagaagaag aaggagcgcc agctggcgga gcagctcgcg   540
gcgaagcacc tgcgcgacga gcagaaccgc aacaaggctc gcaagcagga gctgaagaag   600
cgcgagaagg agcgcgagcg cgcgaggcgc gacgacgctg ctgccgctgc gcagaagaag   660
aaggcggacg ccgcgaagaa gtccgccgcg cctgctgcga gtccgccgc gcctgccgcg   720 aaggctgctg cccccgccac gaaggccgct gctgctgccc cgccacgaa gggtgctgcg   780 ccggtgaaga agtcgaagaa gtaa                                          804

<210> SEQ ID NO 3
<211> LENGTH: 28
<212> TYPE: DNA
<213> ORGANISM: artificial
<220> FEATURE:
<223> OTHER INFORMATION: synthesized

<400> SEQUENCE: 3
```

```
cgggatccat gaccoctctc tccctctc                                          28
```

<210> SEQ ID NO 4
<211> LENGTH: 30
<212> TYPE: DNA
<213> ORGANISM: artificial
<220> FEATURE:
<223> OTHER INFORMATION: synthesized

<400> SEQUENCE: 4

```
cccaagcttt tacttcttcg acttcttcac                                        30
```

<210> SEQ ID NO 5
<211> LENGTH: 250
<212> TYPE: PRT
<213> ORGANISM: Leishmania braziliensis

<400> SEQUENCE: 5

```
Met Val Ser Leu Lys Leu Gln Ala Arg Leu Ala Ser Ser Ile Leu Gly
1               5                   10                  15

Cys Gly Arg Ala Arg Val Trp Leu Asp Pro Asn Glu Ala Met Glu Ile
            20                  25                  30

Gln Asn Ala Asn Ser Arg Lys Ser Val Arg Lys Leu Ile Lys Asp Gly
        35                  40                  45

Phe Ile Ile Arg Lys Pro Val Lys Val His Ser Arg Ala Arg Trp Arg
    50                  55                  60

Lys Met Lys Glu Ala Lys Asp Met Gly Arg His Ser Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Leu Arg Lys Tyr Arg Ala Asp
            100                 105                 110

Lys Lys Ile Asp Arg His Val Tyr Arg Asp Leu Tyr Val Arg Ala Lys
        115                 120                 125

Gly Asn Val Phe Arg Asn Lys Arg Asn Leu Met Glu His Ile His Lys
    130                 135                 140

Ile Lys Asn Glu Lys Lys Glu Arg Gln Leu Ala Glu Gln Leu Ala
145                 150                 155                 160

Ala Lys His Gln Arg Asp Glu Gln His Arg Asn Lys Ala Arg Lys Gln
                165                 170                 175

Glu Leu Lys Lys Arg Glu Lys Glu Arg Glu Arg Ala Arg Arg Asp Asp
            180                 185                 190

Ala Ala Ala Ala Gln Lys Lys Ala Asp Val Ala Lys Lys Ser
        195                 200                 205

Ala Ala Pro Ala Thr Lys Ala Ala Val Ser Ala Lys Ala Ala
    210                 215                 220

Ala Val Ser Val Ser Arg Ala Ala Ala Val Ala Pro Ala Lys
225                 230                 235                 240

Pro Ala Val Pro Ala Lys Lys Ser Lys Lys
                245                 250
```

<210> SEQ ID NO 6
<211> LENGTH: 753
<212> TYPE: DNA
<213> ORGANISM: Leishmania braziliensis

<400> SEQUENCE: 6

-continued

```
atggtgtctc tgaagctgca ggctcgcctc gcgtcgagca tcctcggctg cggccgcgcc    60
cgcgtgtggc tggaccccaa cgaggcgatg gagatccaga cgcaaactc gcgcaagagc    120
gtgcgcaagc tgatcaagga tggcttcatc attcgtaagc cggtgaaggt gcactcgcgc    180
gcgcggtggc gtaagatgaa ggaggcgaag gacatggggc gccacagcgg cgttggccgg    240
cgcgagggta gccgcgaggc ccgcatgccg agcaaggagc tgtggatgcg ccgcctgcgc    300
attctgcgtc gcctgctgcg caagtaccgc gcggacaaga gatcgaccg ccacgtgtac    360
cgcgacctgt acgtgcgcgc gaagggtaac gtgttccgca caagcgcaa ccttatggag    420
cacatccaca gatcaagaa cgagaagaag aaggagcggc agctggcgga gcagcttgcg    480
gcgaagcacc agcgcgacga gcagcaccgc aacaaggctc gcaagcagga gctgaagaag    540
cgcgagaagg agcgcgagcg cgcgaggcgc gacgacgctg ctgctgctgc gcagaagaag    600
aaggcggacg ttgcgaagaa gtctgctgcc cctgctacga aggctgctgc tgtctccgcc    660
gcgaaggctg ctgctgtctc cgtctcgagg gctgctgctg ctgtggctcc cgctgcgaag    720
cctgctgtgc cggcgaagaa gtcgaagaag taa                                 753
```

<210> SEQ ID NO 7
<211> LENGTH: 271
<212> TYPE: PRT
<213> ORGANISM: Leishmania braziliensis

<400> SEQUENCE: 7

```
Met Val Ser Leu Lys Leu Gln Ala Arg Leu Ala Ser Ser Ile Leu Gly
1               5                   10                  15

Cys Gly Arg Ala Arg Val Trp Leu Asp Pro Asn Glu Ala Met Glu Ile
                20                  25                  30

Gln Asn Ala Asn Ser Arg Lys Ser Val Arg Lys Leu Ile Lys Asp Gly
            35                  40                  45

Phe Ile Ile Arg Lys Pro Val Lys Val His Ser Arg Ala Arg Trp Arg
        50                  55                  60

Lys Met Lys Glu Ala Lys Asp Met Gly Arg His Ser Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Leu Arg Lys Tyr Arg Ala Asp
            100                 105                 110

Lys Lys Ile Asp Arg His Val Tyr Arg Asp Leu Tyr Val Arg Ala Lys
        115                 120                 125

Gly Asn Val Phe Arg Asn Lys Arg Asn Leu Met Glu His Ile His Lys
    130                 135                 140

Ile Lys Asn Glu Lys Lys Lys Glu Arg Gln Leu Ala Glu Gln Leu Ala
145                 150                 155                 160

Ala Lys His Gln Arg Asp Glu Gln His Arg Asn Lys Ala Arg Lys Gln
                165                 170                 175

Glu Leu Lys Lys Arg Glu Lys Glu Arg Glu Arg Ala Arg Arg Asp Asp
            180                 185                 190

Ala Ala Ala Ala Ala Gln Lys Lys Lys Ala Asp Val Ala Lys Lys Ser
        195                 200                 205

Ala Ala Pro Ala Thr Lys Ala Ala Val Ser Ala Ala Lys Ala Ala
    210                 215                 220

Ala Val Ser Ala Ala Lys Ala Ala Val Ser Val Ser Arg Ala Ala
225                 230                 235                 240
```

Ala Ala Val Ala Pro Ala Ala Lys Pro Ala Val Pro Ala Lys Ala Ala
            245                 250                 255

Ala Pro Ala Ala Lys Gly Ala Val Pro Ala Lys Lys Ser Lys Lys
        260                 265                 270

<210> SEQ ID NO 8
<211> LENGTH: 816
<212> TYPE: DNA
<213> ORGANISM: Leishmania braziliensis

<400> SEQUENCE: 8

```
atggtgtctc tgaagctgca ggctcgcctc gcgtcgagca tcctcggctg cggccgcgcc      60
cgcgtgtggc tggaccccaa cgaggcgatg gagatccaga cgcaaactc gcgcaagagc     120
gtgcgcaagc tgatcaagga tggcttcatc attcgtaagc cggtgaaggt gcactcgcgc     180
gcgcggtggc gtaagatgaa ggaggcgaag acatggggc gccacagcgg cgttggccgg     240
cgcgagggta gccgcgaggc ccgcatgccg agcaaggagc tgtggatgcg ccgcctgcgc     300
attctgcgtc gcctgctgcg caagtaccgc gcggacaaga agatcgaccg ccacgtgtac     360
cgcgacctgt acgtgcgcgc gaagggtaac gtgttccgca acaagcgcaa ccttatggag     420
cacatccaca gatcaagaa cgagaagaag aaggagcggc agctggcgga gcagcttgcg     480
gcgaagcacc agcgcgacga gcagcaccgc aacaaggctc gcaagcagga gctgaagaag     540
cgcgagaagg agcgcgagcg cgcgaggcgc gacgacgctg ctgctgctgc gcagaagaag     600
aaggcggacg ttgcgaagaa gtctgctgcc ctgctacga aggctgctgc tgtctccgcc     660
gcgaaggctg ctgctgtctc cgccgcgaag gctgctgctg tctccgtctc gagggctgct     720
gctgctgtgg ctcccgctgc gaagcctgct gtgccggcga aggctgcggc gcctgctgcg     780
aagggtgctg tgccggcgaa gaagtcgaag aagtaa                               816
```

<210> SEQ ID NO 9
<211> LENGTH: 176
<212> TYPE: PRT
<213> ORGANISM: Leishmania braziliensis

<400> SEQUENCE: 9

Met Arg Arg Leu Arg Ile Leu Arg Arg Leu Leu Arg Lys Tyr Arg Ala
1               5                   10                  15

Asp Lys Lys Ile Asp Arg His Val Tyr Arg Asp Leu Tyr Val Arg Ala
            20                  25                  30

Lys Gly Asn Val Phe Arg Asn Lys Arg Asn Leu Met Glu His Ile His
        35                  40                  45

Lys Ile Lys Asn Glu Lys Lys Lys Glu Arg Gln Leu Ala Glu Gln Leu
    50                  55                  60

Ala Ala Lys His Gln Arg Asp Glu Gln His Arg Asn Lys Ala Arg Lys
65                  70                  75                  80

Gln Glu Leu Lys Lys Arg Glu Lys Glu Arg Glu Arg Ala Arg Arg Asp
                85                  90                  95

Asp Ala Ala Ala Ala Ala Gln Lys Lys Lys Ala Asp Val Ala Lys Lys
            100                 105                 110

Ser Ala Ala Pro Ala Thr Lys Ala Ala Val Ser Ala Ala Lys Ala
        115                 120                 125

Ala Ala Val Ser Ala Ala Lys Ala Ala Ala Val Ser Val Ser Arg Ala
    130                 135                 140

Ala Ala Ala Val Ala Pro Ala Ala Lys Pro Ala Val Pro Ala Lys Ala
145                 150                 155                 160

Ala Ala Pro Ala Ala Lys Gly Ala Val Pro Ala Lys Lys Ser Lys Lys
            165                 170                 175

<210> SEQ ID NO 10
<211> LENGTH: 531
<212> TYPE: DNA
<213> ORGANISM: Leishmania braziliensis

<400> SEQUENCE: 10
atgcgccgcc tgcgcattct gcgtcgcctg ctgcgcaagt accgcgcgga caagaagatc      60
gaccgccacg tgtaccgcga cctgtacgtg cgcgcgaagg gtaacgtgtt ccgcaacaag     120
cgcaacctta tggagcacat ccacaagatc aagaacgaga agaagaagga gcggcagctg     180
gcggagcagc ttgcggcgaa gcaccagcgc gacgagcagc accgcaacaa ggctcgcaag     240
caggagctga agaagcgcga aggagcgc gagcgcgcga ggcgcgacga cgctgctgct     300
gctgcgcaga agaagaaggc ggacgttgcg aagaagtctg ctgcccctgc tacgaaggct     360
gctgctgtct ccgccgcgaa ggctgctgct gtctccgccg cgaaggctgc tgctgtctcc     420
gtctcgaggg ctgctgctgc tgtggctccc gctgcgaagc ctgctgtgcc ggcgaaggct     480
gcggcgcctg ctgcgaaggg tgctgtgccg gcgaagaagt cgaagaagta a             531

<210> SEQ ID NO 11
<211> LENGTH: 245
<212> TYPE: PRT
<213> ORGANISM: Leishmania infantum

<400> SEQUENCE: 11

Met Val Ser Leu Lys Leu Gln Ala Arg Leu Ala Ser Ser Ile Leu Gly
1               5                   10                  15

Cys Gly Arg Ala Arg Val Trp Leu Asp Pro Asn Glu Ala Val Glu Ile
            20                  25                  30

Gln Asn Ala Asn Ser Arg Lys Ser Val Arg Lys Leu Ile Lys Asp Gly
        35                  40                  45

Phe Ile Ile Arg Lys Pro Val Lys Val His Ser Arg Ala Arg Trp Arg
    50                  55                  60

Lys Met Lys Glu Ala Lys Asp Met Gly Arg His Asn Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Leu Arg Lys Tyr Arg Ala Asp
            100                 105                 110

Lys Lys Ile Asp Arg His Val Tyr Arg Asp Leu Tyr Val Arg Ala Lys
        115                 120                 125

Gly Asn Val Phe Arg Asn Lys Arg Asn Leu Val Glu His Ile His Lys
    130                 135                 140

Ile Lys Asn Glu Lys Lys Lys Glu Arg Gln Leu Ala Glu Gln Leu Ala
145                 150                 155                 160

Ala Lys His Leu Arg Asp Glu Gln Asn Arg Asn Lys Ala Arg Lys Gln
                165                 170                 175

Glu Leu Arg Lys Arg Glu Lys Glu Arg Glu Arg Ala Arg Arg Asp Asp
            180                 185                 190

Ala Ala Ala Ala Ala Gln Lys Lys Lys Ala Asp Ala Leu Lys Lys Ser
        195                 200                 205

Ala Ala Pro Ala Ala Lys Ser Ala Ala Pro Ala Ala Lys Ser Ala Ala
    210                 215                 220

```
Pro Ala Ala Lys Val Ala Ala Pro Ala Thr Lys Gly Ala Ala Pro Val
225                 230                 235                 240

Lys Lys Ser Lys Lys
            245
```

<210> SEQ ID NO 12
<211> LENGTH: 738
<212> TYPE: DNA
<213> ORGANISM: Leishmania infantum

<400> SEQUENCE: 12

```
atggtgtctc tgaagctgca ggctcgcctt gcgtcgagca tcctcggctg cggccgcgcc      60
cgcgtgtggc tggaccccaa cgaggcggtg gagatccaga cgcgaactc gcgcaagagc     120
gtgcgcaagc tgatcaagga tggcttcatc atccgcaagc cggtgaaggt gcactcgcgc     180
gcgcggtggc gtaaaatgaa ggaggcgaag acatggggc ccacaacgg cgttggccgc      240
cgcgagggta gccgcgaggc ccgcatgccg agcaaggagt tgtggatgcg ccgcctgcgc     300
attctgcgcc gcctgctgcg caagtaccgc gcggacaaga gatcgaccg ccacgtgtac     360
cgagacctgt acgtgcgcgc gaagggtaat gtgttccgca acaagcgcaa ccttgtggag     420
cacatccaca agatcaagaa tgagaagaag aaggagcgcc agctggcgga gcagcttgcg     480
gcgaagcacc tgcgcgacga gcagaaccgc aacaaggctc gcaagcagga gctgaggaag     540
cgcgagaagg agcgcgagcg cgcgaggcgc gacgacgctg ctgccgctgc gcagaagaag     600
aaggcggacg ccgcgaagaa gtctgccgcg cctgccgcga gtctgccgc gcctgccgcg     660
aagtctgccg cgcctgccgc gaaggttgct gccccgcca cgaagggtgc tgcgccggtg     720
aagaagtcga agaagtaa                                                  738
```

<210> SEQ ID NO 13
<211> LENGTH: 238
<212> TYPE: PRT
<213> ORGANISM: Leishmania infantum

<400> SEQUENCE: 13

```
Met Val Ser Leu Lys Leu Gln Ala Arg Leu Ala Ser Ser Ile Leu Gly
1               5                   10                  15

Cys Gly Arg Ala Arg Val Trp Leu Asp Pro Asn Glu Ala Val Glu Ile
            20                  25                  30

Gln Asn Ala Asn Ser Arg Lys Ser Val Arg Lys Leu Ile Lys Asp Gly
        35                  40                  45

Phe Ile Ile Arg Lys Pro Val Lys Val His Ser Arg Ala Arg Trp Arg
    50                  55                  60

Lys Met Lys Glu Ala Lys Asp Met Gly Arg His Asn Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Arg Lys Tyr Arg Ala Asp
            100                 105                 110

Lys Lys Ile Asp Arg His Val Tyr Arg Asp Leu Tyr Val Arg Ala Lys
        115                 120                 125

Gly Asn Val Phe Arg Asn Lys Arg Asn Leu Val Glu His Ile His Lys
    130                 135                 140

Ile Lys Asn Glu Lys Lys Lys Glu Arg Gln Leu Ala Glu Gln Leu Ala
145                 150                 155                 160
```

```
Ala Lys His Leu Arg Asp Glu Gln Asn Arg Asn Lys Ala Arg Lys Gln
            165                 170                 175

Glu Leu Arg Lys Arg Glu Lys Glu Arg Glu Ala Arg Asp Asp
        180                 185                 190

Ala Ala Ala Ala Gln Lys Lys Ala Asp Ala Lys Lys Ser
        195                 200                 205

Ala Ala Pro Ala Ala Lys Ser Ala Ala Pro Ala Ala Lys Val Ala Ala
        210                 215                 220

Pro Ala Thr Lys Gly Ala Ala Pro Val Lys Lys Ser Lys Lys
225                 230                 235
```

<210> SEQ ID NO 14
<211> LENGTH: 717
<212> TYPE: DNA
<213> ORGANISM: Leishmania infantum

<400> SEQUENCE: 14

```
atggtgtctc tgaagctgca ggctcgcctt gcgtcgagca tcctcggctg cggccgcgcc    60
cgcgtgtggc tggaccccaa cgaggcggtg gagatccaga cgcgaactc gcgcaagagc    120
gtgcgcaagc tgatcaagga tggcttcatc atccgcaagc cggtgaaggt gcactcgcgc    180
gcgcggtggc gtaaaatgaa ggaggcgaag acatggggc gccacaacgg cgttggccgc    240
cgcgagggta gccgcgaggc ccgcatgccg agcaaggagt tgtggatgcg ccgcctgcgc    300
attctgcgcc gcctgctgcg caagtaccgc gcggacaaga agatcgaccg ccacgtgtac    360
cgagacctgt acgtgcgcgc gaagggtaat gtgttccgca acaagcgcaa ccttgtggag    420
cacatccaca gatcaagaa tgagaagaag aaggagcgcc agctggcgga gcagcttgcg    480
gcgaagcacc tgcgcgacga gcagaaccgc aacaaggctc gcaagcagga gctgaggaag    540
cgcgagaagg agcgcgagcg cgcgaggcgc gacgacgctg ctgccgctgc gcagaagaag    600
aaggcggacg ccgcgaagaa gtctgccgcg cctgccgcga gtctgccgc gcctgccgcg    660
aaggttgctg cccccgccac gaagggtgct gcgccggtga agaagtcgaa gaagtaa      717
```

<210> SEQ ID NO 15
<211> LENGTH: 247
<212> TYPE: PRT
<213> ORGANISM: Leishmania mexicana

<400> SEQUENCE: 15

```
Met Val Ser Leu Lys Leu Gln Ala Arg Leu Ala Ser Ser Ile Leu Ser
1               5                   10                  15

Cys Gly Arg Ala Arg Val Trp Leu Asp Pro Asn Glu Ala Met Glu Ile
            20                  25                  30

Gln Asn Ala Asn Ser Arg Lys Ser Val Arg Lys Leu Ile Lys Asp Gly
        35                  40                  45

Phe Ile Ile Arg Lys Pro Val Lys Val His Ser Arg Ala Arg Trp Arg
    50                  55                  60

Lys Met Lys Glu Ala Lys Asp Met Gly Arg His Asn Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Leu Arg Lys Tyr Arg Ala Asp
            100                 105                 110

Lys Lys Ile Asp Arg His Val Tyr Arg Asp Leu Tyr Met Arg Ala Lys
        115                 120                 125
```

```
Gly Asn Val Phe Arg Asn Lys Arg Asn Leu Val Glu Tyr Ile His Lys
        130                 135                 140
Ile Lys Asn Glu Lys Lys Lys Ala Arg Gln Leu Ala Glu Gln Leu Ala
145                 150                 155                 160
Ala Lys His Leu Arg Asp Glu Gln Asn Arg Asn Lys Ala Arg Lys Gln
                165                 170                 175
Glu Leu Arg Lys Arg Glu Lys Glu Arg Ala Lys Arg Asp Asp
            180                 185                 190
Ala Ala Ala Ala Ala Gln Lys Lys Ala Asp Ala Ala Lys Lys Ser
                195                 200                 205
Ala Ala Pro Ala Ala Lys Ser Ala Ala Pro Ala Ala Lys Ala Ala Ala
        210                 215                 220
Pro Val Ala Lys Ala Ala Ala Ala Pro Ala Ala Lys Gly Ala Ala
225                 230                 235                 240
Pro Val Lys Lys Ser Lys Lys
            245
```

<210> SEQ ID NO 16
<211> LENGTH: 744
<212> TYPE: DNA
<213> ORGANISM: Leishmania mexicana

<400> SEQUENCE: 16

```
atggtgtctc tgaagctgca agctcggctt gcgtcgagca tcctcagctg cggccgcgcc      60
cgcgtgtggc tggaccccaa cgaggcgatg gagatccaga cgcgaactc gcgcaagagc     120
gtgcgcaagc tgatcaagga tggcttcatc atccgcaagc cggtgaaggt gcactcgcgc     180
gcgcggtggc gtaaaatgaa ggaggcgaag acatggggc ccacaacgg cgttggccgc      240
cgcgagggta gccgcgaggc ccgcatgccg agcaaggagt tgtggatgcg ccgcctgcgc     300
attctgcgcc gcctgctgcg caagtaccgc gcggacaaga gatcgaccg ccacgtgtac     360
cgagacctgt acatgcgcgc gaagggtaac gtgttccgca acaagcgcaa ccttgtggag     420
tacatccaca agatcaagaa tgagaagaag aaggcgcgcc agctggcgga gcagcttgcg     480
gcgaagcacc tgcgcgacga gcagaaccgc aacaaggctc gcaagcagga gctgcggaag     540
cgcgagaagg agcgcgagcg cgccgaagcgc gacgacgctg ctgccgctgc gcagaagaag     600
aaggcggacg ccgcgaagaa gtccgccgcg cctgctgcga gtccgccgc gcctgccgcg     660
aaggctgctg cccccgtcgc gaaggccgct gctgctgccc ccgcggcgaa gggtgctgcg     720
ccggtgaaga agtcgaagaa gtaa                                            744
```

<210> SEQ ID NO 17
<211> LENGTH: 247
<212> TYPE: PRT
<213> ORGANISM: Leishmania mexicana

<400> SEQUENCE: 17

```
Met Val Ser Leu Lys Leu Gln Ala Arg Leu Ala Ser Ser Ile Leu Ser
1               5                   10                  15
Cys Gly Arg Ala Arg Val Trp Leu Asp Pro Asn Glu Ala Met Glu Ile
            20                  25                  30
Gln Asn Ala Asn Ser Arg Lys Ser Val Arg Lys Leu Ile Lys Asp Gly
        35                  40                  45
Phe Ile Ile Arg Lys Pro Val Lys Val His Ser Arg Ala Arg Trp Arg
    50                  55                  60
Lys Met Lys Glu Ala Lys Asp Met Gly Arg His Asn Gly Val Gly Arg
```

65                    70                    75                    80
Arg Glu Gly Ser Arg Glu Ala Arg Met Pro Ser Lys Glu Leu Trp Met
                85                    90                    95

Arg Arg Leu Arg Ile Leu Arg Arg Leu Leu Arg Lys Tyr Arg Ala Asp
            100                   105                   110

Lys Lys Ile Asp Arg His Val Tyr Arg Asp Leu Tyr Met Arg Ala Lys
            115                   120                   125

Gly Asn Val Phe Arg Asn Lys Arg Asn Leu Val Glu Tyr Ile His Lys
        130                   135                   140

Ile Lys Asn Glu Lys Lys Ala Arg Gln Leu Ala Glu Gln Leu Ala
145                 150                   155                   160

Ala Lys His Leu Arg Asp Glu Gln Asn Arg Asn Lys Ala Arg Lys Gln
                165                   170                   175

Glu Leu Arg Lys Arg Glu Lys Glu Arg Glu Arg Ala Lys Arg Asp Asp
            180                   185                   190

Ala Ala Ala Ala Ala Gln Lys Lys Ala Asp Ala Ala Lys Lys Ser
            195                   200                   205

Ala Ala Pro Ala Ala Lys Ser Ala Ala Pro Ala Ala Lys Ala Ala Ala
        210                   215                   220

Pro Val Ala Lys Ala Ala Ala Ala Pro Ala Ala Lys Gly Ala Ala
225                   230                   235                   240

Pro Val Lys Lys Ser Lys Lys
            245

<210> SEQ ID NO 18
<211> LENGTH: 744
<212> TYPE: DNA
<213> ORGANISM: Leishmania mexicana

<400> SEQUENCE: 18
atggtgtctc tgaagctgca agctcggctt gcgtcgagca tcctcagctg cggccgcgcc     60
cgcgtgtggc tggaccccaa cgaggcgatg gagatccaga acgcgaactc gcgcaagagc    120
gtgcgcaagc tgatcaagga tggcttcatc atccgcaagc cggtgaaggt gcactcgcgc    180
gcgcggtggc gtaaaatgaa ggaggcgaag gacatggggc gccacaacgg cgttggccgc    240
cgcgagggta ccgcgaggc ccgcatgccg agcaaggagt tgtggatgcg ccgcctgcgc    300
attctgcgcc gcctgctgcg caagtaccgc gcggacaaga gatcgaccg ccacgtgtac    360
cgagacctgt acatgcgcgc gaagggtaac gtgttccgca caagcgcaa ccttgtggag    420
tacatccaca gatcaagaa tgagaagaag aaggcgcgcc agctggcgga gcagcttgcg    480
gcgaagcacc tgcgcgacga gcagaaccgc aacaaggctc gcaagcagga gctgcggaag    540
cgcgagaagg agcgcgagcg cgcgaagcgc gacgacgctg ctgccgctgc gcagaagaag    600
aaggcggacg ccgcgaagaa gtccgccgcg cctgctgcga gtccgccgc gcctgccgcg    660
aaggctgctg cccccgtcgc gaaggccgct gctgctgccc ccgcggcgaa gggtgctgcg    720
ccggtgaaga agtcgaagaa gtaa                                           744

<210> SEQ ID NO 19
<211> LENGTH: 245
<212> TYPE: PRT
<213> ORGANISM: Leishmania donovani

<400> SEQUENCE: 19

Met Val Ser Leu Lys Leu Gln Ala Arg Leu Ala Ser Ser Ile Leu Gly
1               5                   10                  15

Cys Gly Arg Ala Arg Val Trp Leu Asp Pro Asn Glu Ala Val Glu Ile
            20                  25                  30

Gln Asn Ala Asn Ser Arg Lys Ser Val Arg Lys Leu Ile Lys Asp Gly
        35                  40                  45

Phe Ile Ile Arg Lys Pro Val Lys Val His Ser Arg Ala Arg Trp Arg
50                  55                  60

Lys Met Lys Glu Ala Lys Asp Met Gly Arg His Asn Gly Val Gly Arg
65                  70                  75                  80

Arg Glu Gly Ser Arg Glu Ala Arg Met Pro Ser Lys Glu Leu Trp Met
                85                  90                  95

Arg Arg Leu Arg Ile Leu Arg Arg Leu Leu Arg Lys Tyr Arg Ala Asp
            100                 105                 110

Lys Lys Ile Asp Arg His Val Tyr Arg Asp Leu Tyr Val Arg Ala Lys
        115                 120                 125

Gly Asn Val Phe Arg Asn Lys Arg Asn Leu Val Glu His Ile His Lys
130                 135                 140

Ile Lys Asn Glu Lys Lys Lys Glu Arg Gln Leu Ala Glu Gln Leu Ala
145                 150                 155                 160

Ala Lys His Leu Arg Asp Glu Gln Asn Arg Asn Lys Ala Arg Lys Gln
                165                 170                 175

Glu Leu Arg Lys Arg Glu Lys Glu Arg Glu Arg Ala Arg Arg Asp Asp
            180                 185                 190

Ala Ala Ala Ala Ala Gln Lys Lys Lys Ala Asp Ala Lys Lys Lys Ser
        195                 200                 205

Ala Ala Ser Ala Ala Lys Ser Ala Ala Pro Ala Ala Lys Ser Ala Ala
210                 215                 220

Pro Ala Ala Lys Val Ala Ala Pro Ala Thr Lys Gly Ala Ala Pro Val
225                 230                 235                 240

Lys Lys Ser Lys Lys
                245

<210> SEQ ID NO 20
<211> LENGTH: 738
<212> TYPE: DNA
<213> ORGANISM: Leishmania donovani

<400> SEQUENCE: 20
atggtgtctc tgaagctgca ggctcgcctt gcgtcgagca tcctcggctg cggccgcgcc     60
cgcgtgtggc tggaccccaa cgaggcggtg gagatccaga atgcgaactc gcgcaagagc    120
gtgcgcaagc tgatcaagga tggcttcatc atccgcaagc cggtgaaggt gcactcgcgc    180
gcgcggtggc gtaaaatgaa ggaggcgaag gacatggggc gccacaacgg cgttggccgc    240
cgcgagggta gccgcgaggc ccgcatgccg agcaaggagt tgtggatgcg ccgcctgcgc    300
attctgcgcc gcctgctgcg caagtaccgc gcggacaaga gatcgaccg ccacgtgtac    360 cgagacctgt acgtgcgcgc gaagggtaat gtgttccgca acaagcgcaa ccttgtggag    420
cacatccaca gatcaagaa tgagaagaag aaggagcgcc agctggcgga gcagcttgcg    480
gcgaagcacc tgcgcgacga gcagaaccgc aacaaggctc gcaagcagga gctgaggaag    540
cgcgagaagg agcgcgagcg cgcgaggcgc gacgacgctg ctgccgctgc gcagaagaag    600 aaggcgacg ccgcgaagaa gtctgccgcg tctgctgcga agtctgccgc gcctgctgcg    660
aagtctgccg cgcctgccgc gaaggttgct gccccgcca cgaagggtgc tgcgccggtg    720
aagaagtcga agaagtaa                                                  738

<210> SEQ ID NO 21
<211> LENGTH: 372
<212> TYPE: PRT
<213> ORGANISM: Trypanosoma cruzi

<400> SEQUENCE: 21

Met Val Ser Leu Lys Leu Gln Ala Arg Leu Ala Ala Asp Ile Leu Arg
1               5                   10                  15

Cys Gly Arg His Arg Val Trp Leu Asp Pro Asn Glu Ala Ser Glu Ile
            20                  25                  30

Ser Asn Ala Asn Ser Arg Lys Ser Val Arg Lys Leu Ile Lys Asp Gly
        35                  40                  45

Leu Ile Ile Arg Lys Pro Val Lys Val His Ser Arg Ser Arg Trp Arg
    50                  55                  60

His Met Lys Glu Ala Lys Ser Met Gly Arg His Glu Gly Ala Gly Arg
65                  70                  75                  80

Arg Glu Gly Thr Arg Glu Ala Arg Met Pro Ser Lys Glu Leu Trp Met
                85                  90                  95

Arg Arg Leu Arg Ile Leu Arg Arg Leu Leu Arg Lys Tyr Arg Glu Glu
            100                 105                 110

Lys Lys Ile Asp Arg His Ile Tyr Arg Glu Leu Tyr Val Lys Ala Lys
        115                 120                 125

Gly Asn Val Phe Arg Asn Lys Arg Asn Leu Met Glu His Ile His Lys
    130                 135                 140

Val Lys Asn Glu Lys Lys Lys Glu Arg Gln Leu Ala Glu Gln Leu Ala
145                 150                 155                 160

Ala Lys Arg Leu Lys Asp Glu Gln His Arg His Lys Ala Arg Lys Gln
                165                 170                 175

Glu Leu Arg Lys Arg Glu Lys Asp Arg Glu Arg Ala Arg Arg Glu Asp
            180                 185                 190

Ala Ala Ala Ala Ala Ala Lys Gln Lys Ala Ala Lys Lys Ala
        195                 200                 205

Ala Ala Pro Ser Gly Lys Lys Ser Ala Lys Ala Thr Ala Pro Ala
    210                 215                 220

Lys Ala Ala Ala Pro Ala Lys Ala Ala Ala Pro Ala Lys Ala
225                 230                 235                 240

Ala Ala Pro Ala Lys Ala Ala Pro Ala Lys Ala Ala Ala
            245                 250                 255

Ala Pro Ala Lys Ala Ala Thr Ala Pro Ala Lys Ala Ala Ala Pro
        260                 265                 270

Ala Lys Ala Ala Thr Ala Pro Ala Lys Ala Ala Ala Pro Ala Lys
    275                 280                 285

Ala Ala Ala Pro Ala Lys Ala Ala Thr Ala Pro Ala Lys Ala Ala
        290                 295                 300

Ala Ala Pro Ala Lys Ala Ala Thr Ala Pro Ala Lys Ala Ala Ala Ala
305                 310                 315                 320

Pro Ala Lys Ala Ala Thr Ala Pro Ala Lys Ala Ala Ala Ala Pro Ala
                325                 330                 335

Lys Ala Ala Ala Ala Pro Ala Lys Ala Ala Thr Ala Pro Ala Lys Ala
            340                 345                 350

Ala Thr Ala Pro Ala Lys Ala Ala Thr Ala Pro Val Gly Lys Lys Ala
        355                 360                 365

Gly Gly Lys Lys

<210> SEQ ID NO 22
<211> LENGTH: 1119
<212> TYPE: DNA
<213> ORGANISM: Trypanosoma cruzi

<400> SEQUENCE: 22

| | | | | | |
|---|---|---|---|---|---|
| atggtgtcgc | tgaagctgca | ggctcgtttg | gcggcggaca | ttctccgctg | cggtcgccac | 60 |
| cgtgtgtggc | tggatcctaa | tgaggcctct | gagatttcca | atgcaaactc | gcgcaagagc | 120 |
| gtgcgcaagt | tgatcaagga | tggtctgatt | attcgcaagc | ctgtcaaggt | gcactcgcgc | 180 |
| tcccgctggc | gccacatgaa | ggaggcgaag | agcatgggcc | gccacgaggg | cgctgggcgc | 240 |
| cgcgagggta | cccgcgaagc | ccgcatgccg | agcaaggagc | tgtggatgcg | ccgtctgcgc | 300 |
| attctccgcc | gcctgctgcg | caagtaccgc | gaggagaaga | agattgaccg | ccacatctac | 360 |
| cgcgagctgt | acgtgaaggc | gaaggggaac | gtgtttcgca | acaagcgtaa | cctcatggag | 420 |
| cacatccaca | aggtgaagaa | cgagaagaag | aaggaaaggc | agctggctga | gcagctcgcg | 480 |
| gcgaagcgcc | tgaaggatga | gcagcaccgt | cacaaggccc | gcaagcagga | gctgcgtaag | 540 |
| cgcgagaagg | accgcgagcg | tgcgcgtcgc | gaagatgctg | ccgctgccgc | cgccgcgaag | 600 |
| cagaaagctg | ctgcgaagaa | ggccgctgct | ccctctggca | agaagtccgc | gaaggctgct | 660 |
| actgcacctg | cgaaggccgc | tgctgcacct | gcgaaggccg | ctgctgcacc | tgcgaaggct | 720 |
| gctgctgcac | ctgcgaaggc | tgctgctgca | cctgcgaagg | ctgctgctgc | acctgcgaag | 780 |
| gctgctactg | cacctgcgaa | ggccgctgct | gcacctgcga | aggctgctac | tgcacctgcg | 840 |
| aaggccgctg | ctgcacctgc | gaaggctgct | gctgcacctg | cgaaggctgc | tactgcacct | 900 |
| gcgaaggccg | ctgctgcacc | tgcgaaggct | gctactgcac | ctgcgaaggc | cgctgctgca | 960 |
| cctgcgaagg | ctgctactgc | acctgcgaag | gccgctgctg | cacctgcgaa | ggccgctgct | 1020 |
| gcacctgcga | aggctgctac | tgcacctgcg | aaggccgcta | ctgcacctgc | gaaggctgct | 1080 |
| actgcacccg | ttggaaagaa | ggctggtggc | aagaagtga | | | 1119 |

<210> SEQ ID NO 23
<211> LENGTH: 356
<212> TYPE: PRT
<213> ORGANISM: Trypanosoma cruzi

<400> SEQUENCE: 23

Met Val Ser Leu Lys Leu Gln Ala Arg Leu Ala Ala Asp Ile Leu Arg
1               5                   10                  15

Cys Gly Arg His Arg Val Trp Leu Asp Pro Asn Glu Ala Ser Glu Ile
                20                  25                  30

Ser Asn Ala Asn Ser Arg Lys Ser Val Arg Lys Leu Ile Lys Asp Gly
            35                  40                  45

Leu Ile Ile Arg Lys Pro Val Lys Val His Ser Arg Ser Arg Trp Arg
        50                  55                  60

His Met Lys Glu Ala Lys Ser Met Gly Arg His Glu Gly Ala Gly Arg
65                  70                  75                  80

Arg Glu Gly Thr Arg Glu Ala Arg Met Pro Ser Lys Glu Leu Trp Met
                85                  90                  95

Arg Arg Leu Arg Ile Leu Arg Arg Leu Leu Arg Lys Tyr Arg Glu Glu
                100                 105                 110

Lys Lys Ile Asp Arg His Ile Tyr Arg Glu Leu Tyr Val Lys Ala Lys
            115                 120                 125

Gly Asn Val Phe Arg Asn Lys Arg Asn Leu Met Glu His Ile His Lys
    130                 135                 140

Val Lys Asn Glu Lys Lys Lys Glu Arg Gln Leu Ala Glu Gln Leu Ala
145                 150                 155                 160

Ala Lys Arg Leu Lys Asp Glu Gln His Arg His Lys Ala Arg Lys Gln
                165                 170                 175

Glu Leu Arg Lys Arg Glu Lys Asp Arg Glu Arg Ala Arg Arg Glu Asp
            180                 185                 190

Ala Ala Ala Ala Ala Ala Ala Lys Gln Lys Ala Ala Lys Lys Ala
        195                 200                 205

Ala Ala Pro Ser Gly Lys Lys Ser Ala Lys Ala Ala Pro Ala Lys
    210                 215                 220

Ala Ala Ala Ala Pro Ala Lys Ala Ala Ala Pro Pro Ala Lys Thr Ala
225                 230                 235                 240

Ala Ala Pro Ala Lys Ala Ala Pro Ala Lys Ala Ala Ala Pro Pro
        245                 250                 255

Ala Lys Ala Ala Ala Pro Pro Ala Lys Thr Ala Ala Pro Pro Ala Lys
        260                 265                 270

Thr Ala Ala Pro Pro Ala Lys Ala Ala Ala Pro Pro Ala Lys Ala Ala
        275                 280                 285

Ala Pro Pro Ala Lys Ala Ala Ala Pro Pro Ala Lys Ala Ala Ala Ala
    290                 295                 300

Pro Ala Lys Ala Ala Ala Ala Pro Ala Lys Ala Ala Ala Pro Ala
305                 310                 315                 320

Lys Ala Ala Ala Pro Pro Ala Lys Ala Ala Ala Pro Pro Ala Lys Ala
                325                 330                 335

Ala Ala Pro Pro Ala Lys Ala Ala Ala Ala Pro Val Gly Lys Lys Ala
        340                 345                 350

Gly Gly Lys Lys
    355

<210> SEQ ID NO 24
<211> LENGTH: 1071
<212> TYPE: DNA
<213> ORGANISM: Trypanosoma cruzi

<400> SEQUENCE: 24
atggtgtcgc tgaagctgca ggctcgtttg gcggcggaca ttctccgctg cggtcgccac      60
cgtgtgtggc tggaccctaa tgaggcctct gagatttcca atgcaaactc gcgcaagagc     120
gtgcgcaagt tgatcaagga tggtctgatt attcgcaagc ctgtcaaggt gcactcgcgc     180
tcccgctggc gccacatgaa ggaggcgaag agcatgggcc gccacgaggg cgctgggcgc     240
cgcgagggta cccgcgaagc ccgcatgccg agcaaggagc tgtggatgcg ccgtctcgcg     300
attctccgcc gcctgctgcg caagtaccgc gaggagaaga gattgaccg ccacatttac     360 cgcgagctgt acgtgaaggc gaaggggaac gtgtttcgca acaagcgtaa cctcatggag     420
cacatccaca aggtgaagaa cgagaagaag aaggaaaggc agctggctga gcagctcgcg     480
gcgaagcgcc tgaaggatga gcagcaccgt cacaaggccc gcaagcagga gctgcgtaag     540
cgcgagaagg accgcgagcg tgcgcgtcgc gaagatgctg ccgctgccgc cgccgcgaag     600
cagaaagctg ctgcgaagaa ggccgctgct ccctctggca agaagtccgc gaaggctgct     660
gcacccgcga aggctgctgc tgcacccgcg aaggccgctc tccaccgcgc gaagaccgct     720
gctgcacccg cgaaggctgc tgcacctgcc aaggctgctg ctccaccgcg cgaaggctgct     780

```
gctccacccg cgaagaccgc tgctccaccc gcgaagaccg ctgctccacc cgcgaaggct      840
gctgctccac ccgcgaaggc cgctgctcca cccgcgaagg ccgctgctcc acccgcgaag      900
gccgctgctg cacccgcgaa ggccgctgct gcacccgcga aggctgctgc tccacccgcg      960
aaggccgctg ctccacccgc gaaggctgct gctccacccg cgaaggctgc tgctccaccc     1020
gcgaaggctg ctgctgctcc cgttggaaag aaggctggtg gcaagaagtg a             1071
```

<210> SEQ ID NO 25
<211> LENGTH: 343
<212> TYPE: PRT
<213> ORGANISM: Trypanosoma cruzi

<400> SEQUENCE: 25

```
Met Val Ser Leu Lys Leu Gln Ala Arg Leu Ala Asp Ile Leu Arg
1               5                  10                  15

Cys Gly Arg His Arg Val Trp Leu Asp Pro Asn Glu Ala Ser Glu Ile
            20                  25                  30

Ser Asn Ala Asn Ser Arg Lys Ser Val Arg Lys Leu Ile Lys Asp Gly
        35                  40                  45

Leu Ile Ile Arg Lys Pro Val Lys Val His Ser Arg Ser Arg Trp Arg
50                  55                  60

His Met Lys Glu Ala Lys Ser Met Gly Arg His Glu Gly Ala Gly Arg
65                  70                  75                  80

Arg Glu Gly Thr Arg Glu Ala Arg Met Pro Ser Lys Glu Leu Trp Met
                85                  90                  95

Arg Arg Leu Arg Ile Leu Arg Arg Leu Leu Arg Lys Tyr Arg Glu Glu
            100                 105                 110

Lys Lys Ile Asp Arg His Ile Tyr Arg Glu Leu Tyr Val Lys Ala Lys
        115                 120                 125

Gly Asn Val Phe Arg Asn Lys Arg Asn Leu Met Glu His Ile His Lys
    130                 135                 140

Val Lys Asn Glu Lys Lys Lys Glu Arg Gln Leu Ala Glu Gln Leu Ala
145                 150                 155                 160

Ala Lys Arg Leu Lys Asp Glu Gln His Arg His Lys Ala Arg Lys Gln
                165                 170                 175

Glu Leu Arg Lys Arg Glu Lys Asp Arg Glu Arg Ala Arg Arg Glu Asp
            180                 185                 190

Ala Ala Ala Ala Ala Ala Ala Lys Gln Lys Ala Ala Lys Lys Ala
        195                 200                 205

Ala Ala Pro Ser Gly Lys Lys Ser Ala Lys Ala Ala Ile Ala Pro Ala
    210                 215                 220

Lys Ala Ala Ala Ala Pro Ala Lys Ala Ala Ala Ala Pro Ala Lys Ala
225                 230                 235                 240

Ala Ala Ala Pro Ala Lys Ala Ala Ala Pro Ala Lys Ala Ala Ala
                245                 250                 255

Ala Pro Ala Lys Ala Ala Thr Ala Pro Ala Lys Ala Ala Ala Ala Pro
            260                 265                 270

Ala Lys Thr Ala Ala Ala Pro Ala Lys Ala Ala Ala Pro Ala Lys Ala
        275                 280                 285

Ala Ala Pro Ala Lys Ala Ala Thr Ala Pro Ala Lys Ala Ala Ala
    290                 295                 300

Ala Pro Ala Lys Ala Ala Thr Ala Pro Ala Lys Ala Ala Thr Ala Pro
305                 310                 315                 320
```

Ala Lys Ala Ala Ala Ala Pro Ala Lys Ala Ala Thr Ala Pro Val Gly
                325                 330                 335

Lys Lys Ala Gly Gly Lys Lys
        340

<210> SEQ ID NO 26
<211> LENGTH: 1032
<212> TYPE: DNA
<213> ORGANISM: Trypanosoma cruzi

<400> SEQUENCE: 26

```
atggtgtcgc tgaagctgca ggctcgtttg gcggcggaca ttctccgctg cggtcgccac      60
cgtgtgtggc tggaccctaa tgaggcctct gagatttcca atgcaaactc cgcaagagc     120
gtgcgcaagt tgatcaagga tggtctgatt attcgcaagc ctgtcaaggt gcactcgcgc     180
tcccgctggc gccacatgaa ggaggcgaag agcatgggcc gccacgaggg cgctgggcgc     240
cgcgagggta cccgcgaagc ccgcatgccg agcaaggagc tgtggatgcg ccgtctgcgc     300
attctccgcc gctgctgcg caagtaccgc gaggagaaga gattgaccg ccacatctac      360
cgcgagctgt acgtgaaggc gaaggggaac gtgtttcgca acaagcgtaa cctcatggag     420
cacatccaca aggtgaagaa cgagaagaag aaggaaaggc agctggctga cagctcgcg      480
gcgaagcgcc tgaaggatga gcagcaccgt cacaaggccc gcaagcagga gctgcgtaag     540
cgcgagaagg accgcgagcg tgcgcgtcgc gaagatgctg ccgctgccgc cgccgcgaag     600
cagaaagctg ctgcgaagaa ggccgctgct ccctctggca agaagtccgc gaaggctgct     660
attgcacctg cgaaggccgc tgctgcacct gcgaaggccg ctgctgcacc tgcgaaggct     720
gctgctgcac ctgcgaaggc cgctgctgca cctgcgaagg ctgctgctgc acctgcgaag     780
gctgctactg cacctgcgaa ggctgctgct gcacctgcca agaccgctgc tgcacctgcg     840
aaggctgctg cacctgcgaa ggccgctgct gcacctgcga aggccgctac tgcacctgcg     900
aaggctgctg ctgcacctgc gaaggccgct actgcacctg cgaaggctgc tactgcacct     960
gcgaaggctg ctgctgcacc tgcgaaggcc gctactgcac ccgttggaaa aaggctggt    1020
ggcaagaagt ga                                                        1032
```

<210> SEQ ID NO 27
<211> LENGTH: 357
<212> TYPE: PRT
<213> ORGANISM: Trypanosoma cruzi

<400> SEQUENCE: 27

Met Val Ser Leu Lys Leu Gln Ala Arg Leu Ala Ala Asp Ile Leu Arg
1               5                   10                  15

Cys Gly Arg His Arg Val Trp Leu Asp Pro Asn Glu Ala Ser Glu Ile
            20                  25                  30

Ser Asn Ala Asn Ser Arg Lys Ser Val Arg Lys Leu Ile Lys Asp Gly
        35                  40                  45

Leu Ile Ile Arg Lys Pro Val Lys Val His Ser Arg Ser Arg Trp Arg
    50                  55                  60

His Met Lys Glu Ala Lys Ser Met Gly Arg His Glu Gly Ala Gly Arg
65                  70                  75                  80

Arg Glu Gly Thr Arg Glu Ala Arg Met Pro Ser Lys Glu Leu Trp Met
                85                  90                  95

Arg Arg Leu Arg Ile Leu Arg Arg Leu Leu Arg Lys Tyr Arg Glu Glu
            100                 105                 110

```
Lys Lys Ile Asp Arg His Ile Tyr Arg Glu Leu Tyr Val Lys Ala Lys
            115                 120                 125
Gly Asn Val Phe Arg Asn Lys Arg Asn Leu Met Glu His Ile His Lys
        130                 135                 140
Val Lys Asn Glu Lys Lys Lys Glu Arg Gln Leu Ala Glu Gln Leu Ala
145                 150                 155                 160
Ala Lys Arg Leu Lys Asp Glu Gln His Arg His Lys Ala Arg Lys Gln
                165                 170                 175
Glu Leu Arg Lys Arg Glu Lys Asp Arg Glu Arg Ala Arg Arg Glu Asp
            180                 185                 190
Ala Ala Ala Ala Ala Ala Lys Gln Lys Ala Ala Lys Lys Ala
        195                 200                 205
Ala Ala Pro Ser Gly Lys Lys Ser Ala Lys Ala Ala Pro Ala Lys
    210                 215                 220
Ala Ala Ala Ala Pro Ala Lys Thr Ala Ala Pro Ala Lys Ala Ala
225                 230                 235                 240
Ala Pro Pro Ala Lys Ala Ala Pro Pro Ala Lys Ala Ala Pro
                245                 250                 255
Pro Ala Lys Ala Ala Ala Pro Pro Ala Lys Ala Ala Pro Pro Ala
            260                 265                 270
Lys Ala Ala Ala Pro Pro Ala Lys Ala Ala Pro Pro Ala Lys Ala
        275                 280                 285
Ala Ala Pro Pro Ala Lys Ala Ala Ala Pro Ala Lys Thr Ala Ala
    290                 295                 300
Pro Pro Ala Lys Ala Ala Ala Pro Ala Lys Thr Ala Ala Pro Pro
305                 310                 315                 320
Ala Lys Thr Ala Ala Pro Pro Ala Lys Ala Ala Thr Pro Pro Ala Lys
                325                 330                 335
Ala Ala Ala Pro Pro Ala Lys Ala Ala Ala Pro Val Gly Lys Lys
            340                 345                 350
Ala Gly Gly Lys Lys
        355

<210> SEQ ID NO 28
<211> LENGTH: 1074
<212> TYPE: DNA
<213> ORGANISM: Trypanosoma cruzi

<400> SEQUENCE: 28
atggtgtcgc tgaagctgca ggctcgtttg gcggcggaca ttctccgctg cggtcgccac      60
cgtgtgtggc tggaccctaa tgaggcctct gagatttcca atgcaaactc gcgcaagagc     120
gtgcgcaagt tgatcaagga tggtctgatt attcgcaagc tgtcaaggt gcactcgcgc     180 tcccgctggc gccacatgaa ggaggcgaag agcatgggcc gccacgaggg cgctgggcgc     240
cgcgagggta cccgcgaagc ccgcatgccg agcaaggagc tgtggatgcg ccgtctgcgc     300
attctccgcc gcctgctgcg caagtaccgc gaggagaaga gattgaccg ccacatttac     360 cgcgagctgt acgtgaaggc gaaggggaac gtgtttcgca caagcgtaa cctcatggag     420 cacatccaca aggtgaagaa cgagaagaag aaggaaggc agctggctga cagctcgcg     480 gcgaagcgcc tgaaggatga cagcaccgt cacaaggccc gcaagcagga gctgcgtaag     540
cgcgagaagg accgcgagcg tgcgcgtcgc gaagatgctg ccgctgccgc cgccgcgaag     600
cagaaagctg ctgcgaagaa ggccgctgct ccctctggca gaagtccgc gaaggctgct     660 gcacctgcca aggctgctgc tgcacccgcg aagaccgctg ctccaccgc gaaggccgct     720
```

```
gctccacccg cgaaggctgc tgctccaccc gcgaaggctg ctgctccacc cgcgaaggct    780
gctgctccac ccgcgaaggc tgctgctcca cccgcgaagg ctgctgctcc acccgcgaag    840
gctgctgctc acccgcgaaa ggctgctgct ccacccgcga aggctgctgc tgcacccgcg    900
aagaccgctg ctccacccgc gaaggctgct gctgcacccg cgaagaccgc tgctccaccc    960
gcgaagaccg ctgctccacc cgcgaaggcc gctactccac ccgcgaaggc tgctgctcca   1020
cccgcgaagg ctgctgctgc tcccgttgga agaaggctg tggcaagaa gtga          1074

<210> SEQ ID NO 29
<211> LENGTH: 260
<212> TYPE: PRT
<213> ORGANISM: Trypanosoma brucei

<400> SEQUENCE: 29

Met Val Ser Leu Lys Leu Gln Ala Arg Leu Ala Ala Asp Ile Leu Arg
1               5                   10                  15

Cys Gly Arg Gly Arg Val Trp Leu Asp Pro Asn Glu Ala Val Glu Ile
                20                  25                  30

Arg Asn Ala Asn Ser Arg Lys Ser Val Arg Lys Leu Ile Lys Asp Gly
            35                  40                  45

Leu Val Met Arg Lys Pro Val Lys Val His Ser Arg Ser Arg Trp Arg
        50                  55                  60

Gln Met Lys Leu Ala Lys Ser Met Gly Arg His Glu Gly Thr Gly Arg
65                  70                  75                  80

Arg Glu Gly Thr Arg Glu Ala Arg Met Pro Ser Lys Asp Leu Trp Met
                85                  90                  95

Arg Arg Leu Arg Ile Leu Arg Arg Leu Leu Arg Lys Tyr Arg Glu Glu
                100                 105                 110

Lys Lys Ile Asp Arg His Ile Tyr Arg Glu Leu Tyr Met Lys Ala Lys
            115                 120                 125

Gly Asn Val Phe Arg Asn Lys Arg Asn Leu Met Glu His Ile His Lys
        130                 135                 140

Val Lys Asn Glu Lys Lys Lys Ala Arg Gln Leu Ala Glu Gln Leu Ala
145                 150                 155                 160

Ala Lys Arg Leu Lys Asp Glu Gln Asn Arg Arg Lys Ala Arg Lys Gln
                165                 170                 175

Glu Leu Lys Lys Arg Glu Lys Glu Arg Glu Arg Ala Arg Arg Asp Asp
                180                 185                 190

Ala Ala Ala Ala Ala Ala Lys Gln Arg Ala Ala Lys Lys Ala
            195                 200                 205

Ala Ala Pro Ala Ala Lys Lys Gly Gly Lys Ala Val Ala Pro Ala Thr
        210                 215                 220

Pro Ala Lys Ala Ala Pro Ala Lys Ala Ala Ala Lys Val Ala Pro
225                 230                 235                 240

Ala Lys Ala Ala Pro Ala Lys Ala Ala Ser Pro Ala Gly Lys Lys Ala
                245                 250                 255

Ala Gly Lys Lys
        260

<210> SEQ ID NO 30
<211> LENGTH: 783
<212> TYPE: DNA
<213> ORGANISM: Trypanosoma brucei

<400> SEQUENCE: 30
```

```
atggtgtcac tgaagctcca agctcgcctg gcagcggaca tcctgcgctg cggccgcggc    60
cgcgtgtggt tggaccctaa cgaagcagta gagattcgca atgccaattc acgcaagagt   120
gtacgcaagt tgatcaaaga cggtttggta atgcgaaagc ctgttaaggt gcattcgcgc   180
tcccgctggc gccagatgaa gttggcgaag agcatgggac gccacgaggg taccggccgc   240
cgcgagggta ctcgcgaagc acgcatgccc agcaaggacc tttggatgcg ccgacttcgc   300
attcttcgcc gtttgcttcg caagtaccgc gaagaaaaga gattgatcg gcacatctac    360 cgcgagctgt acatgaaggc aaagggcaac gtgttccgca acaagcgcaa ccttatggag   420
cacatccaca aggtgaagaa cgagaagaag aaggctcgtc agcttgctga gcaactcgcg   480
gcgaaacgcc taaaggacga gcagaaccgc cgcaaggcac gaaagcagga gctgaagaag   540
cgtgagaagg aacgtgagcg tgcacgccgt gacgatgccg ctgctgctgc cgctgccaaa   600
caacgagctg ccgcgaagaa ggctgccgct cccgctgcca gaagggtgg caaggctgtt    660 gccccgcca ctcctgcgaa ggccgcccct gcaaaggccg ccgctgcgaa ggttgcccca   720
gcgaaggcgg ctcccgcaaa ggccgccagc cctgccggga agaaggcagc gggtaagaag   780
tga                                                                  783

<210> SEQ ID NO 31
<211> LENGTH: 20
<212> TYPE: PRT
<213> ORGANISM: artificial
<220> FEATURE:
<223> OTHER INFORMATION: synthesized

<400> SEQUENCE: 31

Met Thr Pro Leu Ser Leu Ser Ser Ser Arg His Ser Phe Lys Gln Asn
1               5                   10                  15

Glu Thr Gln Asn
            20

<210> SEQ ID NO 32
<211> LENGTH: 20
<212> TYPE: PRT
<213> ORGANISM: artificial
<220> FEATURE:
<223> OTHER INFORMATION: synthesized

<400> SEQUENCE: 32

Ser Phe Lys Gln Asn Glu Thr Gln Asn Met Val Ser Leu Lys Leu Gln
1               5                   10                  15

Ala Arg Leu Ala
            20

<210> SEQ ID NO 33
<211> LENGTH: 20
<212> TYPE: PRT
<213> ORGANISM: artificial
<220> FEATURE:
<223> OTHER INFORMATION: synthesized

<400> SEQUENCE: 33

Ser Leu Lys Leu Gln Ala Arg Leu Ala Ser Ser Ile Leu Gly Cys Gly
1               5                   10                  15

Arg Ala Arg Val
            20

<210> SEQ ID NO 34
```

```
<211> LENGTH: 20
<212> TYPE: PRT
<213> ORGANISM: artificial
<220> FEATURE:
<223> OTHER INFORMATION: synthesized

<400> SEQUENCE: 34

Ile Leu Gly Cys Gly Arg Ala Arg Val Trp Leu Asp Pro Asn Glu Ala
1               5                   10                  15

Val Glu Ile Gln
            20

<210> SEQ ID NO 35
<211> LENGTH: 20
<212> TYPE: PRT
<213> ORGANISM: artificial
<220> FEATURE:
<223> OTHER INFORMATION: synthesized

<400> SEQUENCE: 35

Asp Pro Asn Glu Ala Val Glu Ile Gln Asn Ala Asn Ser Arg Lys Ser
1               5                   10                  15

Val Arg Lys Leu
            20

<210> SEQ ID NO 36
<211> LENGTH: 20
<212> TYPE: PRT
<213> ORGANISM: artificial
<220> FEATURE:
<223> OTHER INFORMATION: synthesized

<400> SEQUENCE: 36

Asn Ser Arg Lys Ser Val Arg Lys Leu Ile Lys Asp Gly Phe Ile Ile
1               5                   10                  15

Arg Lys Pro Val
            20

<210> SEQ ID NO 37
<211> LENGTH: 20
<212> TYPE: PRT
<213> ORGANISM: artificial
<220> FEATURE:
<223> OTHER INFORMATION: synthesized

<400> SEQUENCE: 37

Asp Gly Phe Ile Ile Arg Lys Pro Val Lys Val His Ser Arg Ala Arg
1               5                   10                  15

Trp Arg Lys Met
            20

<210> SEQ ID NO 38
<211> LENGTH: 20
<212> TYPE: PRT
<213> ORGANISM: artificial
<220> FEATURE:
<223> OTHER INFORMATION: synthesized

<400> SEQUENCE: 38

His Ser Arg Ala Arg Trp Arg Lys Met Lys Glu Ala Lys Asp Met Gly
1               5                   10                  15

Arg His Asn Gly
            20
```

<210> SEQ ID NO 39
<211> LENGTH: 20
<212> TYPE: PRT
<213> ORGANISM: artificial
<220> FEATURE:
<223> OTHER INFORMATION: synthesized

<400> SEQUENCE: 39

Ala Lys Asp Met Gly Arg His Asn Gly Val Gly Arg Arg Glu Gly Ser
1               5                   10                  15

Arg Glu Ala Arg
            20

<210> SEQ ID NO 40
<211> LENGTH: 20
<212> TYPE: PRT
<213> ORGANISM: artificial
<220> FEATURE:
<223> OTHER INFORMATION: synthesized

<400> SEQUENCE: 40

Arg Arg Glu Gly Ser Arg Glu Ala Arg Met Pro Ser Lys Glu Leu Trp
1               5                   10                  15

Met Arg Arg Leu
            20

<210> SEQ ID NO 41
<211> LENGTH: 20
<212> TYPE: PRT
<213> ORGANISM: artificial
<220> FEATURE:
<223> OTHER INFORMATION: synthesized

<400> SEQUENCE: 41

Ser Lys Glu Leu Trp Met Arg Arg Leu Arg Ile Leu Arg Arg Leu Leu
1               5                   10                  15

Arg Lys Tyr Arg
            20

<210> SEQ ID NO 42
<211> LENGTH: 20
<212> TYPE: PRT
<213> ORGANISM: artificial
<220> FEATURE:
<223> OTHER INFORMATION: synthesized

<400> SEQUENCE: 42

Leu Arg Arg Leu Leu Arg Lys Tyr Arg Ala Asp Lys Lys Ile Asp Arg
1               5                   10                  15

His Val Tyr Arg
            20

<210> SEQ ID NO 43
<211> LENGTH: 20
<212> TYPE: PRT
<213> ORGANISM: artificial
<220> FEATURE:
<223> OTHER INFORMATION: synthesized

<400> SEQUENCE: 43

Lys Lys Ile Asp Arg His Val Tyr Arg Asp Leu Tyr Met Arg Ala Lys
1               5                   10                  15

Gly Asn Val Phe
            20

```
<210> SEQ ID NO 44
<211> LENGTH: 20
<212> TYPE: PRT
<213> ORGANISM: artificial
<220> FEATURE:
<223> OTHER INFORMATION: synthesized

<400> SEQUENCE: 44

Tyr Met Arg Ala Lys Gly Asn Val Phe Arg Asn Lys Arg Asn Leu Val
1               5                   10                  15

Glu His Ile His
            20

<210> SEQ ID NO 45
<211> LENGTH: 20
<212> TYPE: PRT
<213> ORGANISM: artificial
<220> FEATURE:
<223> OTHER INFORMATION: synthesized

<400> SEQUENCE: 45

Lys Arg Asn Leu Val Glu His Ile His Lys Ile Lys Asn Glu Lys Lys
1               5                   10                  15

Lys Glu Arg Gln
            20

<210> SEQ ID NO 46
<211> LENGTH: 20
<212> TYPE: PRT
<213> ORGANISM: artificial
<220> FEATURE:
<223> OTHER INFORMATION: synthesized

<400> SEQUENCE: 46

Lys Asn Glu Lys Lys Lys Glu Arg Gln Leu Ala Glu Gln Leu Ala Ala
1               5                   10                  15

Lys His Leu Arg
            20

<210> SEQ ID NO 47
<211> LENGTH: 20
<212> TYPE: PRT
<213> ORGANISM: artificial
<220> FEATURE:
<223> OTHER INFORMATION: synthesized

<400> SEQUENCE: 47

Glu Gln Leu Ala Ala Lys His Leu Arg Asp Glu Gln Asn Arg Asn Lys
1               5                   10                  15

Ala Arg Lys Gln
            20

<210> SEQ ID NO 48
<211> LENGTH: 20
<212> TYPE: PRT
<213> ORGANISM: artificial
<220> FEATURE:
<223> OTHER INFORMATION: synthesized

<400> SEQUENCE: 48

Gln Asn Arg Asn Lys Ala Arg Lys Gln Glu Leu Lys Lys Arg Glu Lys
1               5                   10                  15

Glu Arg Glu Arg
            20
```

<210> SEQ ID NO 49
<211> LENGTH: 20
<212> TYPE: PRT
<213> ORGANISM: artificial
<220> FEATURE:
<223> OTHER INFORMATION: synthesized

<400> SEQUENCE: 49

Lys Lys Arg Glu Lys Glu Arg Glu Arg Ala Arg Arg Asp Asp Ala Ala
1               5                   10                  15

Ala Ala Ala Gln
            20

<210> SEQ ID NO 50
<211> LENGTH: 20
<212> TYPE: PRT
<213> ORGANISM: artificial
<220> FEATURE:
<223> OTHER INFORMATION: synthesized

<400> SEQUENCE: 50

Arg Asp Asp Ala Ala Ala Ala Ala Gln Lys Lys Lys Ala Asp Ala Ala
1               5                   10                  15

Lys Lys Ser Ala
            20

<210> SEQ ID NO 51
<211> LENGTH: 20
<212> TYPE: PRT
<213> ORGANISM: artificial
<220> FEATURE:
<223> OTHER INFORMATION: synthesized

<400> SEQUENCE: 51

Lys Ala Asp Ala Ala Lys Lys Ser Ala Ala Pro Ala Ala Lys Ser Ala
1               5                   10                  15

Ala Pro Ala Ala
            20

<210> SEQ ID NO 52
<211> LENGTH: 20
<212> TYPE: PRT
<213> ORGANISM: artificial
<220> FEATURE:
<223> OTHER INFORMATION: synthesized

<400> SEQUENCE: 52

Ala Ala Lys Ser Ala Ala Pro Ala Ala Lys Ala Ala Ala Pro Ala Thr
1               5                   10                  15

Lys Ala Ala Ala
            20

<210> SEQ ID NO 53
<211> LENGTH: 20
<212> TYPE: PRT
<213> ORGANISM: artificial
<220> FEATURE:
<223> OTHER INFORMATION: synthesized

<400> SEQUENCE: 53

Ala Ala Pro Ala Thr Lys Ala Ala Ala Ala Pro Ala Thr Lys Gly
1               5                   10                  15

Ala Ala Pro Val

-continued

```
            20

<210> SEQ ID NO 54
<211> LENGTH: 14
<212> TYPE: PRT
<213> ORGANISM: artificial
<220> FEATURE:
<223> OTHER INFORMATION: synthesized

<400> SEQUENCE: 54

Pro Ala Thr Lys Gly Ala Ala Pro Val Lys Lys Ser Lys Lys
1               5                   10

<210> SEQ ID NO 55
<211> LENGTH: 31
<212> TYPE: PRT
<213> ORGANISM: artificial
<220> FEATURE:
<223> OTHER INFORMATION: synthesized

<400> SEQUENCE: 55

Met Thr Pro Leu Ser Leu Ser Ser Ser Arg His Ser Phe Lys Gln Asn
1               5                   10                  15

Glu Thr Gln Asn Met Val Ser Leu Lys Leu Gln Ala Arg Leu Ala
            20                  25                  30

<210> SEQ ID NO 56
<211> LENGTH: 42
<212> TYPE: PRT
<213> ORGANISM: artificial
<220> FEATURE:
<223> OTHER INFORMATION: synthesized

<400> SEQUENCE: 56

Leu Arg Arg Leu Leu Arg Lys Tyr Arg Ala Asp Lys Lys Ile Asp Arg
1               5                   10                  15

His Val Tyr Arg Asp Leu Tyr Met Arg Ala Lys Gly Asn Val Phe Arg
            20                  25                  30

Asn Lys Arg Asn Leu Val Glu His Ile His
        35                  40

<210> SEQ ID NO 57
<211> LENGTH: 25
<212> TYPE: PRT
<213> ORGANISM: artificial
<220> FEATURE:
<223> OTHER INFORMATION: synthesized

<400> SEQUENCE: 57

Ala Ala Pro Ala Thr Lys Ala Ala Ala Ala Ala Pro Ala Thr Lys Gly
1               5                   10                  15

Ala Ala Pro Val Lys Lys Ser Lys Lys
            20                  25
```

MOLECULE FOR TREATING AN INFLAMMATORY DISORDER

CROSS REFERENCE TO RELATED APPLICATIONS

The present application is the 35 U.S.C. 371 National Stage of International Application Number PCT/EP2012/058453, filed May 8, 2012, which claims the benefit of U.S. Provisional Application No. 61/484,167, filed May 9, 2011 and claims priority from European patent application EP11165248.3, filed May 9, 2011, the contents of each of which are incorporated herein by reference.

SEQUENCE LISTING SUBMISSION VIA EFS-WEB

A computer readable text file, entitled $2^{nd}$ Amended Sequence Listing, created on or about Dec. 18, 2015, with a file size of about 58 KB contains the sequence listing for this application and is hereby incorporated by reference in its entirety.

FIELD OF THE INVENTION

The invention provides a L19 source as a medicament, preferably for preventing or treating an inflammatory disorder in an individual.

BACKGROUND OF THE INVENTION

Immune and related inflammatory diseases are a manifestation of complex, frequently interconnected biological pathways which in normal physiology respond to insult or injury by initiating repair of the insult or injury, and mount an innate and acquired response. Disease or pathology occurs when these physiological pathways cause further insult or injury, either by an exaggerated response caused by an abnormal regulation or overstimulation, or a combination of the two. Despite the advent of new anti-inflammatory drugs such as anti-TNF agents, inflammatory diseases continue to represent an important unmet medical need, often due to a lack of responsiveness and resistance to these drugs.

Immune and related inflammatory diseases that may be modulated by the use of anti-inflammatory agents include Autoimmune Diabetes (any others similar), diabetes mellitus, uveitis, (1) Multiple Sclerosis, Rheumatoid Arthritis (RA), Irritable Bowel Disease (IBD), Irritable Bowel syndrome, ulcerative colitis, Crohn's disease, Controlling Allograft Rejection after organ transplantation, graft versus host disease (GVHD), inflammatory lung diseases including asthma and chronic obstructive pulmonary disease (COPD) (2), cancer (4) systemic lupus erythematosus, SLE, sarcoidosis, cancer and Psoriasis.

RA is considered a systemic autoimmune disease, managed by treatment with Disease-modifying anti-rheumatic drugs (DMARDS), typically in combination, to minimize the side effects associated with systemic drugs. Side effects of these drugs include ulcerative stomatitis, reduced white blood count IBD is a term that describes chronic inflammation disorder of the small and/or large intestine. Included within the area of IBD is ulcerative colitis and Crohn's disease. While the exact causes are not firmly established, IBD is considered to be an autoimmune disease. Currently no cure is available, and treatments are focused on suppressing the abnormal or exaggerated inflammatory response. Treatments include corticosteroids (such as methotrexate, azathioprine, and mercaptopurine) and aminosalicylates. Long term use of corticosteroids are associated with thinning of the bones, infection, cataracts, and love and bone marrow effects. Aminosalicylates tend to be better tolerated, since they are poorly absorbed, and act on the affected area topically. Side effects include headache, and rarely more serious conditions, such as pancreatitis.

Psoriasis is treated in different ways. Use of corticosteroids topically is a common method of treatment, but drawbacks include ineffectiveness and development of resistance. Use of phototherapy is effective in treating psoriasis by increasing apoptosis, implicated in reduced inflammation. Short term drawbacks are increased discomfort, and itching, with long term effects being an increased risk of squamous cell and melanoma skin cancers. Systemic drugs are utilised to treat psoriasis, which have a variety of other, often undesired systemic effects and must be used under close supervision and monitoring by a dermatologist.

Therefore there is still a need to design new treatments for an inflammatory disease such as RA, IBD, and psoriasis which do not have all the drawbacks of existing treatments.

DESCRIPTION OF THE INVENTION

L19 Source

In a first aspect, there is provided a L19 source for use as a medicament.

L19 is a ribosomal protein. Ribosomal proteins are well conserved cytosolic proteins. Therefore, a L19 source may be prepared from any eukaryotic organism, be it plant or animal, be it from mammals, reptiles, fish, insects, or any other chromosome bearing organism, such as protozoa. The invention is not limited to a specific L19 source as long as the encoded L19 protein product is able to induce an anti-inflammatory response as later defined herein. Preferred protozoans include *plasmodium* and in particular members of the trypanosomatid family, more in particular different species of the trypanosomatical protozoan *Leishmania*. There are over 20 known species of *Leishmania*, including species of the subgenus *Leishmania*, comprising the complex *L. major*, including *L. major*, the complex *L. Donovani*, including *L. chagasi*, *L. donovani* and *L. infantum*, the complex *L. Mexicana*, including *L. amazonensis* and *L. mexicana*, as well as the subspecies *Viannia*, comprising the complex *L. braziliensis*, including *L. braziliensis* and *L. peruviana* and the complex *L. guyanensis*, including *L. guyanensis* and *L. panamensis*. Plasmodium species of particular interest are *Plasmodium falciparum* and *Plasmodium vivax*. Alternatively a L19 source may be obtained from a *Trypanosoma* species. A *Trypanosoma* species may be a *Trypanosoma cruzi*, a *Trypanosoma brucei*. In a preferred embodiment, a L19 source is obtained from or derived from or originated from a *Leishmania* species, preferably *Leishmania major*, *Leishmania infantum Leishmania donovani*, *Leishmania chagasi* and/or *Leishmania braziliensis*. More preferred is a L19 source which is obtained from or derived from or originated from *Leishmania major*. The skilled person will understand that a source of L19 may also be prepared by mixing two or more L19 sources derived from the same organism or from several distinct organisms as identified herein. The use of an L19 source has been demonstrated herein to have attractive properties since it has been shown that the encoded L19 protein product is able to induce the production of an anti-inflammatory response in a treated subject.

A preferred L19 source is a nucleic acid molecule, an oligonucleotide, a protein, a protein fragment and/or a peptide each being derived from a L19 protein or polypeptide or nucleic acid molecule as defined herein. A L19 source preferably comprises or consists of a L19 protein, a L19 polypeptide, a L19 derived peptide or a L19 protein fragment and/or a nucleic acid molecule encoding a L19 protein or L19 polypeptide or L19 derived peptide or L19 protein fragment, each has defined herein. A preferred L19 protein is represented by SEQ ID NO:1. This preferred L19 protein is preferably encoded by SEQ ID NO:2. Another preferred L19 protein is represented by SEQ ID NO: 5, 7, 9, 11, 13, 15, 17, 19, 21, 23, 25, 27 or 29. Each of these other L19 proteins is preferably encoded by SEQ ID NO: 6, 8, 10, 12, 14, 16, 18, 20, 22, 24, 26, 28, 30 respectively.

In a first embodiment, a preferred L19 source is a nucleic acid molecule represented by a nucleotide sequence selected from the group consisting of:
i. nucleotide sequences encoding a polypeptide comprising an amino acid sequence that has at least 50% sequence identity or similarity with the amino acid sequence of SEQ ID NO:1, 5, 7, 9, 11, 13, 15, 17, 19, 21, 23, 25, 27 or 29,
ii. nucleotide sequences comprising a nucleotide sequence that has at least 50% sequence identity or similarity with the nucleotide sequence of SEQ ID NO:2, 4, 6, 8, 10, 12, 14, 16, 18, 20, 22, 24, 26, 28 or 30,
iii. nucleotide sequences the complementary strand of which hybridizes to a nucleic acid molecule of sequence of (i) or (ii) and
iv. nucleotide sequences the sequences of which differs from the sequence of a nucleic acid molecule of (iii) due to the degeneracy of the genetic code.

In a second embodiment, a preferred L19 source is a polypeptide encoded by a nucleic acid molecule of the first embodiment as identified above. In a more preferred embodiment, a L19 source is a polypeptide whose amino acid sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or similarity with a polypeptide having amino acid sequence SEQ ID NO:1, 5, 7, 9, 11, 13, 15, 17, 19, 21, 23, 25, 27, 29 or 31.

We identified several L19 proteins and corresponding encoding nucleic acid molecules. Each of these L19 proteins comprises an amino acid sequence having at least 60%, 70%, 80%, 90%, 95% or more with SEQ ID NO:1. Each of the nucleic acid molecule encoding each of these L19 proteins comprises a nucleotide sequence having at least 60%, 70%, 80%, 90%, 95% or more with SEQ ID NO:2. Each of these L19 proteins represents a homologue of Leishmania major L19 protein as represented by SEQ ID NO:1

Briefly, we identified three L19 proteins from Leishmania braziliensis, being represented by SEQ ID NO: 5, 7 or 9. Each of these proteins is preferably encoded by the following nucleotide sequence SEQ ID NO: 6, 8 or 10 respectively.

We also identified two L19 proteins from Leishmania infantum, being represented by SEQ ID NO: 11 or 13. Each of these proteins is preferably encoded by the following nucleotide sequence SEQ ID NO:12 or 14 respectively.

We also identified two L19 proteins from Leishmania mexicana, being represented by SEQ ID NO: 15 or 17. Each of these proteins is preferably encoded by the following nucleotide sequence SEQ ID NO:16 or 18 respectively.

We also identified one L19 protein from Leishmania donovani, being represented by SEQ ID NO: 19. This protein is preferably encoded by the following nucleotide sequence SEQ ID NO:20.

In addition, we identified four L19 proteins from Trypanosoma cruzi, being represented by SEQ ID NO: 21, 23, 25 or 27. Each of these proteins is preferably encoded by the following nucleotide sequence SEQ ID NO: 22, 24, 26 or 28 respectively.

We also identified one L19 protein from Trypanosoma brucei, being represented by SEQ ID NO: 29. This protein is preferably encoded by the following nucleotide sequence SEQ ID NO:30.

Preferably, said amino acid sequence or nucleotide sequence as defined herein having at least 50% identity or similarity with a specific identified amino acid or nucleotide sequence are encompassed by the present invention and are said to be functional when the encoded protein polypeptide, protein fragment or peptide is capable of inducing an anti-inflammatory response as obtainable by the L19 protein represented by SEQ ID NO:1, 5, 7, 9, 11, 13, 15, 17, 19, 21, 23, 25, 27 or 29 to at least some extent. To at least some extent preferably means that at least 50%, at least 60%, 70%, 80%, at least 90% or 100% of the anti-inflammatory response induced by SEQ ID NO:1, 5, 7, 9, 11, 13, 15, 17, 19, 21, 23, 25, 27 or 29.

Inducing an anti-inflammatory response is or is preferably defined as the ability to induce a detectable production of an anti-inflammatory compound and/or the ability to induce a decrease of the production of an inflammatory compound in a treated subject or individual. An anti-inflammatory compound is preferably a cytokine. More preferred cytokine is IL-10. An inflammatory compound is preferably a cytokine. More preferred cytokine IFNγ and/or TNFα. The production of IL-10 or IFNγ or TNFα is preferably assessed at the mRNA level using PCR or at the protein level using ELISA, an ELISPOT or FACS. All these techniques are known to the skilled person. Many publications have implicated the elevation of IL-10 with a reduction in inflammation, as a result of disease. The same holds with the elevation of IFNγ or TNFα and the presence of inflammation. The production of an anti-inflammatory compound may be assessed on a treated subject or on a sample obtained from said subject. In this context, a sample may be a tissue or a fluid or a cell. Preferred tissue includes spleen or skin or intestine or lung. Preferred fluid includes blood. Preferred cells include a PBMC (Peripheral Blood Mononuclear Cell) or skin cells or intestinal cells or lung cells. An anti-inflammatory response may be induced after at least 1, 2, 3, 4, 5, 6, 7 days of treatment with a L19 source. Preferred L19 sources are a L19 polypeptide, protein, protein fragment or peptide. The induction of an anti-inflammatory response may also be an increase of the induction of an anti-inflammatory response. In this context, an "increase" may mean an increase of at least 1%, 5%, 10%, 15%, 20%, 25%, 30%, 35%, 40%, 45%, 50%, 55%, 60%, 65%, 70%, 75%, 80%, 85%, 90%, 95%, 100%. The induction of an anti-inflammatory response may also be the decrease of the amount or quantity of IFNγ and/or TNFα. In this context, a "decrease" may mean a decrease of at least 1%, 5%, 10%, 15%, 20%, 25%, 30%, 35%, 40%, 45%, 50%, 55%, 60%, 65%, 70%, 75%, 80%, 85%, 90%, 95%, 100%.

In a preferred embodiment, an anti-inflammatory compound is produced and no detectable inflammatory compound (i.e. IFNγ and/or TNFα) are detected. In this context, no IFN-γ and/or no TNFα is detected. The absence of TNFα and/or IFN-γ is preferably assessed using PCR or an ELISA.

The absence of an inflammatory compound may be assessed on a treated subject or on a sample obtained from said subject as for the anti-inflammatory compound.

In a preferred assay, an anti-inflammatory response, more preferably the production of IL-10 or an increase of IL-10 is detected after at least 24 hours or 48 hours or 72 hours of incubation of a L19 source, preferably a L19 polypeptide or a L19 peptide with a PBMC. In this preferred assay, a decreased amount of IFN-gamma and/or a decreased amount of TNFα, or no detectable IFN-γ and/or no TNFα is detected after at least 24 hours or 48 hours or 72 hours of incubation of a L19 source, preferably a L19 polypeptide or a L19 peptide with a PBMC. More preferably, IL-10, INFγ and/or TNFα is assessed by ELISA as described in the experimental part. In a further preferred embodiment, a L19 source which is able to induce an anti-inflammatory response is also able to prevent and/or delay the development of an inflammatory disorder or condition or disease and/or is able to alleviate one or more symptom(s) and/or one or more characteristic(s) or parameter(s) of a cell or tissue from a treated subject as later defined herein.

A preferred L19 source is a nucleic acid molecule of the first embodiment as identified above. This preferred nucleic acid molecule is represented by a nucleotide sequence which is derived from SEQ ID NO:2, 4, 6, 8, 10, 12, 14, 16, 18, 20, 22, 24, 26, 28 or 30, or a sequence having at least 50% identity or similarity with SEQ ID NO:2, 4, 6, 8, 10, 12, 14, 16, 18, 20, 22, 24, 26, 28 or 30 or with a part thereof and that may comprise substitutions, insertions, deletions and additional 5' and/or 3' terminal nucleotides or chemical moieties to increase stability, solubility or targeting. In a preferred embodiment, a L19 source is a nucleic acid molecule whose nucleotide sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or similarity with SEQ ID NO:2, 4, 6, 8, 10, 12, 14, 16, 18, 20, 22, 24, 26, 28 or 30 or with a part thereof.

A L19 nucleic acid molecule as defined herein is preferably an oligonucleotide. A preferred oligonucleotide has a length of at least 8, 10, 15, 20, 25, 30, 35, 40, 45, 50, 55, 60, 65, 70, 75, 80, 85, 90, 95, 100 nucleotides and is derived from SEQ ID NO: 2, 4, 6, 8, 10, 12, 14, 16, 18, 20, 22, 24, 26, 28 or 30. More preferred oligonucleotides comprise at least 8, 10, 15, 20, 25, 30, 35, 40, 45, 50, 55, 60, 65, 70, 75, 80, 85, 90, 95, 100 or more contiguous nucleotides of a corresponding L19 nucleic acid molecule as identified above, preferably represented by SEQ ID NO:2, 4, 6, 8, 10, 12, 14, 16, 18, 20, 22, 24, 26, 28 or 30 and whose encoded product is able to induce an anti-inflammatory response as earlier defined herein. In a preferred embodiment, therefore, a L19 nucleic acid molecule as defined herein is preferably an oligonucleotide comprising at least 8, 10, 15, 20, 25, 30, 35, 40, 45, 50, 55, 60, 65, 70, 75, 80, 85, 90, 95, 100 or more contiguous nucleotides of SEQ ID NO:2, 4, 6, 8, 10, 12, 14, 16, 18, 20, 22, 24, 26, 28 or 30.

Accordingly a preferred L19 source is an oligonucleotide comprising at least 8, 10, 15, 20, 25, 30, 35, 40, 45, 50, 55, 60, 65, 70, 75, 80, 85, 90, 95, 100 or more contiguous nucleotides of SEQ ID NO:2.

Another preferred L19 source is a polypeptide encoded by a nucleic acid molecule of the first embodiment as identified above and/or is a polypeptide whose amino acid sequence has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or similarity with a polypeptide having amino acid sequence SEQ ID NO:1, 5, 7, 9, 11, 13, 15, 17, 19, 21, 23, 25, 27 or 29 or with a part thereof.

A preferred polypeptide is represented by an amino acid sequence which is derived from SEQ ID NO:1, 5, 7, 9, 11, 13, 15, 17, 19, 21, 23, 25, 27 or 29 or from a part thereof or a sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity or similarity with SEQ ID NO:1, 5, 7, 9, 11, 13, 15, 17, 19, 21, 23, 25, 27 or 29 or with a part thereof and that may comprise substitutions, insertions, deletions and additional N- or C-terminal amino acids or chemical moieties to increase stability, solubility.

A L19 protein fragment or a L19 derived peptide or a L19 polypeptide or a L19 protein as defined herein is preferably a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 265, or 267 contiguous amino acids of a corresponding L19 protein, preferably represented by SEQ ID NO:1, 5, 7, 9, 11, 13, 15, 17, 19, 21, 23, 25, 27 or 29 and which is able to induce an anti-inflammatory response as earlier defined herein. In a preferred embodiment, therefore, a L19 protein fragment or a L19 derived peptide as defined herein is preferably a fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 265, or 267 contiguous amino acids of SEQ ID NO:1, 5, 7, 9, 11, 13, 15, 17, 19, 21, 23, 25, 27 or 29. A L19 source may also comprise a full length L19 protein such as the one represented by SEQ ID NO:1, 5, 7, 9, 11, 13, 15, 17, 19, 21, 23, 25, 27 or 29 and comprises additional amino acids at the N- and/or C-terminus of the L19 protein. In another preferred embodiment, a L19 source comprises or consists of a protein or a polypeptide comprising at least one protein fragment of a L19 protein. A preferred L19 source is a protein fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 50, 60, 70, 80, 90, 100, 110, 120, 130, 140, 150, 160, 170, 180, 190, 200, 210, 220, 230, 240, 250, 260, 265, or 267 contiguous amino acids of SEQ ID NO:1.

In an embodiment, a source of L19 is a peptide derived from SEQ ID NO:1 or a fragment of SEQ ID NO:1. A preferred fragment or peptide comprises at least 14, 15, 16, 17, 18, 19, 20, 21, 22, 23, 24, 25, 26, 27, 28, 29, 30, 31, 32, 33, 34, 35, 36, 37, 38, 39, 40, 41, 42 contiguous amino acids of SEQ ID NO:1. In example 3, three regions of L19 and specific peptides derived from L19 have been identified as being able of inducing the production of IL-10. The preferred regions of L19 are the following:

Region 1 comprises peptides having SEQ ID NO: 31, 32 and/or 55,

Region 2 comprises peptides having SEQ ID NO: 42, 43, 44 and/or 56,

Region 3 comprises peptides having SEQ ID NO: 53, 54 and/or 57

Below we define in more details these peptides or fragments of SEQ ID NO:1. A protein fragment of SEQ ID NO:1 comprising at least 14 contiguous amino acids of SEQ ID NO:1 and comprising SEQ ID NO: 31, 32, 55, 42, 43, 44, 56, 53, 54 and/or 57.

A more preferred fragment of SEQ ID NO:1 comprises SEQ ID NO:31 or 32 or 42 or 43 or 44 or 53 and comprises up to 40, 39, 38, 37, 36, 35, 34, 33, 32, 31, 30, 29, 28, 27, 26, 25, 24, 23, 22, 21 or 20 contiguous amino acids from SEQ ID NO:1. Said fragment may comprise SEQ ID NO:31 or 32 or 42 or 43 or 44 or 53 and may have a length of up to 40, 39, 38, 37, 36, 35, 34, 33, 32, 31, 30, 29, 28, 27, 26, 25, 24, 23, 22, 21 or 20 amino acids. Said fragment preferably consists of SEQ ID NO:31 or 32 or 42 or 43 or 44 or 53.

Another more preferred fragment of SEQ ID NO:1 comprises SEQ ID NO: 54 and comprises up to 40, 39, 38, 37, 36, 35, 34, 33, 32, 31, 30, 29, 28, 27, 26, 25, 24, 23, 22, 21, 20, 19, 18, 17, 16, 15 or 14 contiguous amino acids from SEQ ID NO:1. Said fragment may comprise SEQ ID NO:54 and may have a length of up to 40, 39, 38, 37, 36, 35, 34, 33, 32, 31, 30, 29, 28, 27, 26, 25, 24, 23, 22, 21, 20, 19, 18, 17, 16, 15 or 14 amino acids. Said fragment preferably consists of SEQ ID NO:54.

A more preferred fragment of SEQ ID NO:1 comprises SEQ ID NO: 57 and comprises up to 40, 39, 38, 37, 36, 35, 34, 33, 32, 31, 30, 29, 28, 27, 26, 25 contiguous amino acids from SEQ ID NO:1. Said fragment may comprise SEQ ID NO: 57 and may have a length of up to 40, 39, 38, 37, 36, 35, 34, 33, 32, 31, 30, 29, 28, 27, 26, 25 amino acids. Said fragment preferably consists of SEQ ID NO: 57.

A more preferred fragment of SEQ ID NO:1 comprises SEQ ID NO: 55 and comprises up to 40, 39, 38, 37, 36, 35, 34, 33, 32, 31 contiguous amino acids from SEQ ID NO:1. Said fragment may comprise SEQ ID NO: 55 and may have a length of up to 40, 39, 38, 37, 36, 35, 34, 33, 32, 31 amino acids. Said fragment preferably consists of SEQ ID NO: 55.

A more preferred fragment of SEQ ID NO:1 comprises SEQ ID NO: 56 and comprises up to 50, 49, 48, 47, 46, 45, 44, 43, 42 contiguous amino acids from SEQ ID NO:1. Said fragment may comprise SEQ ID NO: 56 and may have a length of up to 50, 49, 48, 47, 46, 45, 44, 43, 42 amino acids. Said fragment preferably consists of SEQ ID NO: 56.

Each of the preferred fragments of SEQ ID NO:1 as identified herein is preferably able to induce an anti-inflammatory response as earlier defined herein.

The source of L19 may be a protein, a digest of the protein and/or a fragment thereof, which may be in a purified form or may be comprised within a crude composition, preferably of biological origin, such as a bacterial lysate, yeast lysate, fungal lysate, bacterial supernatant, yeast supernatant, fungal supernatant, sonicate or fixate. Alternatively, a L19 source may be chemically synthesized or enzymatically produced in vitro in a cell free system or in a cellular system. The source of a L19 protein, or fragment thereof, may also be a nucleic acid encoding said, or fragment thereof, from an RNA or DNA template. The RNA or DNA molecules may be 'naked' DNA, preferably comprised in vesicles or liposomes, or they may be comprised in a vector. The vector may be any (recombinant) DNA or RNA vector known in the art, and preferably is a plasmid; wherein genes encoding latency antigens are operably linked to regulatory sequences conferring expression and translation of the encoded messengers. The vector may also be any DNA or RNA virus, such as, but not limited to, Adenovirus, Adeno-Associated Virus (AAV), a retrovirus, a lentivirus, modified Vaccinia Ankara virus (MVA) or Fowl Pox virus, or any other viral vector capable of conferring expression of said polypeptide into a chosen subject. DNA vectors may be non-integrating, such as episomally replicating vectors, or may be vectors integrating in the host genome by random integration or by homologous recombination.

A L19 source or a composition as defined herein for use according to the invention may be suitable for in vitro administration to a cell, a tissue and/or an organ of individuals affected by or at risk of developing an inflammatory disorder, and/or may be suitable for in vivo or ex vivo administration to a cell, a tissue and/or an organ of such individuals and/or may be suitable for in vivo administration to such individuals. Depending on the type of source used (protein-based or nucleic acid-based), the skilled person will know which type of formulation is suited. A L19 source may be administered as such (naked protein or nucleic-acid). Alternatively, a nucleic acid-based source may be administered using a nucleic acid construct as defined herein. Said L19 source or a composition as defined herein may be directly or indirectly in vivo, in vitro or ex vivo administered to a cell, tissue and/or an organ of an individual affected by or at risk of developing an inflammatory disorder or in vivo to such individual. Preferably said cells are cells of an individual suffering from an inflammatory disorder. Preferably said tissue is a tissue of an individual suffering from an inflammatory disorder. Depending on the inflammatory disorder, a given type of cell or tissue may be more suited to be treated with a L19 source or a composition of the invention. For example a tissue may be skin, blood, intestine, lung and suitable cells may be derived from these tissues.

A L19 source or a composition of the invention may be indirectly administered using suitable means known in the art. A nucleic acid molecule as defined in a first embodiment may for example be provided to an individual or a cell, tissue or organ of said individual in the form of an expression vector wherein the expression vector encodes a transcript comprising said nucleic acid molecule. The expression vector is preferably introduced into a cell, tissue, organ or individual via a gene delivery vehicle. In a preferred embodiment, there is provided a viral-based expression vector comprising an expression cassette or a transcription cassette that drives expression or transcription of a molecule as identified herein. A preferred delivery vehicle is a viral vector such as an adeno-associated virus vector (AAV), or a retroviral vector such as a lentivirus vector and the like. Also plasmids, artificial chromosomes, plasmids suitable for targeted homologous recombination and integration in the human genome of cells may be suitably applied for delivery of nucleic acid molecule as defined in a first embodiment.

Improvements in means for providing an individual or a cell, tissue, organ of said individual with a L19 source or a composition as defined herein, are anticipated considering the progress that has already thus far been achieved. When administering a L19 source or a composition, it is preferred that said L19 source or composition is dissolved in a solution that is compatible with the delivery method. For intravenous, subcutaneous, intramuscular, intradermal, intrathecal and/or intraventricular administration it is preferred that the solution is a physiological salt solution.

In the context of the invention, a subject or an individual or a patient or an animal means a human or an animal. An animal which is encompassed within the scope of the invention includes a mammal. Preferred mammals include a dog and a cat.

In a preferred embodiment, at least 1 µg of an L19 source is used to induce an anti-inflammatory response. The ranges of dose of L19 source as given above are preferred doses for in vitro or ex vivo uses. The skilled person will understand that depending on the L19 source used, the cell, tissue, organ or subject to be treated, the medium used and the transfection and incubation conditions, the dose of L19 source used may further vary and may need to be optimised any further.

A L19 source is preferably a medicament or for use as a medicament. More preferably, said medicament is for preventing, delaying, and/or treating an inflammatory disorder to a subject in the need thereof. Within the context of the invention, an inflammatory disorder is any inflammatory disease or condition or any condition wherein inflammation will occur at a given stage. Examples of inflammatory diseases or conditions include, but are not limited to, rheumatoid arthritis (RA), juvenile rheumatoid arthritis, psoriasis, psoriatic arthritis, ankylosing spondylitis, inflammatory bowel disease (IBD) (including Crohn's disease or ulcerative colitis), irritable bowel syndrome, hepatitis, sepsis, alcoholic liver disease, and non-alcoholic steatosis, nephritis, such as glomerular nephritis, asthma, endocarditis, myasthenia gravis, multiple sclerosis, autoimmune diabetes (any others similar), diabetes mellitus, uveitis, (1) controlling allograft rejection after organ transplantation, graft versus host disease (GVHD), inflammatory lung diseases including asthma and chronic obstructive pulmonary disease (COPD) (2), cancer (4) systemic lupus erythematosus, SLE, UV-induced skin inflammation, atopic dermatitis and sarcoidosis.

As used herein, the term "hepatitis" refers to a gastroenterological disease, condition, or disorder that is characterized, at least in part, by inflammation of the liver. Examples of hepatitis include, but are not limited to, hepatitis associated with hepatitis A virus, hepatitis B virus, hepatitis C virus, or liver inflammation associated with ischemia/reperfusion.

In a more preferred embodiment, said medicament is able to alleviate one or more symptom(s) from a treated patient and/or one or more characteristic(s) or parameter(s) of a cell or tissue or organ from a treated patient is/are improved using a L19 source or a composition of the invention. For each inflammatory disease, the skilled person knows at least one symptom, parameter or characteristic, values of said parameter or characteristic associated with said disease and how to assess each of them. If a medicament of the invention is able to induce an anti-inflammatory response as earlier defined herein, said medicament is said to be able to prevent and/or delay the development of an inflammatory disorder or condition or disease and/or to improve one or more characteristic(s) or parameter(s) of a cell or tissue from a treated subject as later defined herein.

Below, we give a parameter specific for Rheumatoid arthritis, psoriasis and inflammatory bowel disease respectively.

Rheumatoid arthritis is a systemic disease and is one of the most common forms of arthritis. It is characterised by inflammation of the membrane lining the joint, causing pain, stiffness, warmth, redness and swelling.

There are several animal models for RA known in the art. One example is the collagen-induced arthritis (CIA) model, in which mice develop chronic inflammatory arthritis that closely resembles human rheumatoid arthritis. Since CIA shares similar immunological and pathological features with RA, this makes it a suitable model for screening potential treatments for RA. In this model, the basic mechanisms of pathogenesis are known with the various immunological and inflammatory parameters relating to immune-mediated arthritis having been determined. These parameters can be used to assess compound efficacy in the CIA model (5).

RA is preferably diagnosed after having assessed the index of Disease Activity Score (DAS) or the related DAS28 (6) including the measurements of several parameters and symptoms on a subject. The assessment of said indexes may be carried out by a clinician examining a subject. In a more preferred embodiment, said medicament is able to alleviate one or more symptom(s) from a treated patient and/or one or more characteristic(s) or parameter(s) of a cell or tissue or organ from a treated patient is/are improved using a L19 source or a composition of the invention when said medicament is able to induce a significant change in DAS or DAS28. Other ways of assessing rheumatoid arthritis are also described in (6) and in (7). A medicament as defined herein is able to improve one parameter if after at least one week, one month, six month, one year or more of treatment using a L19 source or a composition of the invention. Preferably, the value of said parameter has been improved of at least 1%, 2%, 5%, 10% or more by comparison of the value of said parameter before the onset of the treatment.

A medicament as defined herein is able to alleviate one symptom or one characteristic of a patient or of a cell, tissue or organ or said patient if after at least one week, one month, six month, one year or more of treatment using a L19 source or a composition of the invention, said symptom or characteristic is no longer detectable.

Inflammatory Bowel Disease (IBD) is a group of inflammatory conditions of the colon and the small intestine including ulcerative colitis and Crohn's disease. Ulcerative colitis is characterized by inflammation of the colon, resulting in the colon emptying frequently, resulting in diarrhea and associated cramps, fever and weight loss. The lining of the colon becomes damaged, forming ulcers that release mucous, pus and blood. Repeated episodes can result in the formation of scar tissue, and death of colon tissue, or sepsis with severe disease. Current treatments focus on suppressing the abnormal inflammatory process in the colon lining.

A well-characterized animal model for human IBD, ulcerative colitis and especially Crohn's disease is the 2,4,6-trinitrobenzenesulphonic acid/ethanol (TNBS) induced colitis model. Colitis induced by intra-rectal administration of TNBS. This induces a T-cell mediated immune response in the colonic mucosa, leading to a massive mucosal inflammation, characterized by the infiltration of T-cells and macrophages throughout the entire wall of the large bowel. The histopathological nature is accompanied by progressive weight loss, bloody diarrhea, large bowel wall thickening (8). The current animal models of colon inflammation do not fully reflect the complexity of the disease in humans, however, they are valuable tools to evaluate efficacy of therapeutic compounds.

Psoriasis is a common, chronic skin disease, in which new skin cells grow abnormally resulting in inflamed, swollen and scaly patches of skin, where the old skin has not shed quickly enough. The most common form is plaque psoriasis, characterised by lesions topped with silvery white scales. Psoriasis may be limited to a few lesions, or may involve extensive areas of skin, most commonly appearing on the elbows, knees, scalp and trunk. Mild cases of psoriasis are managed by topical applications. However, more severe cases require ultraviolet therapy, which is inconvenient or the use of systemic immunosuppressive therapies, which, due to toxic side effects, are often of limited value in long term use. In addition, psoriasis frequently recurs, including shortly after stopping immunosuppressive therapy.

Several disease models have been developed for the evaluation of potential disease modulators. One such model is an in vivo xenograft model for psoriasis with human psoriatic skin implanted into a severe immune deficient (SCID) mouse. Therapies that abolish, or reduce the inflammation can be tested by administration to the SCID mice, baring human inflammatory tissue. Efficacy of treatment can be assessed by a range of indices. Psoriasis is a disease that is preferably diagnosed after having assessed the index of Psoriasis Area and Severity Index (PASI), physician global assessment (PGA) (9) or NPF Psoriasis Score (NPF-PS), including the measurements of several parameters and symptoms on a subject. The assessment of said indexes may be carried out by a clinician examining a subject. In a more preferred embodiment, said medicament is able to alleviate one or more symptom(s) from a treated patient and/or one or more characteristic(s) or parameter(s) of a cell or tissue or organ from a treated patient is/are improved using a L19 source or a composition of the invention when said medicament is able to induce a significant change in PASI, PGA or NPF-PS. Other ways of assessing psoriasis include the Dermatology Life Quality Index (DLQI) (10) and the Salford Psoriasis Index (SPI) also described in (11) A medicament as defined herein is able to improve one parameter if after at least one week, one month, six month, one year or more of treatment using a L19 source or a composition of the invention. Preferably, the value of said parameter has been improved of at least 1%, 2%, 5%, 10% or more by comparison of the value of said parameter before the onset of the treatment.

A medicament as defined herein is able to alleviate one symptom or one characteristic of a patient or of a cell, tissue or organ or said patient if after at least one week, one month, six month, one year or more of treatment using a L19 source or a composition of the invention, said symptom or characteristic is no longer detectable.

A preferred L19 source as defined herein is for preventing or treating an inflammatory disorder in an individual. An individual which may be treated using such L19 source may already have been diagnosed as having an inflammatory disorder. Alternatively an individual which may be treated using such L19 source may not have yet been diagnosed as having an inflammatory disorder but may be an individual having an increased risk of developing an inflammatory disorder in the future given his or her genetic background. A preferred individual is a human being.

Composition

In a further aspect, there is provided a composition comprising a L19 source as defined herein. In a preferred embodiment, said composition being preferably a pharmaceutical composition said pharmaceutical composition comprising a pharmaceutically acceptable carrier, salt, diluent and/or excipient.

Such a pharmaceutical composition may comprise any pharmaceutically acceptable carrier, filler, salt, preservative, solubilizer, diluent and/or excipient is also provided. Such pharmaceutically acceptable carrier, filler, salt, preservative, solubilizer, diluent and/or excipient may for instance be found in (12). Each feature of said composition has earlier been defined herein.

If several L19 sources are used, dose as defined herein may refer to the total dose of all L19 sources used or the dose of each L19 source used or added. Therefore in one embodiment, there is provided a composition wherein each or the total amount of L19 source used is dosed in an amount from 0.1 mg/kg and 100 mg/kg.

Particularly preferred in the invention is the use of an excipient that will aid in delivery of each of the constituents as defined herein to a cell and/or into a cell. Preferred are excipients capable of forming complexes, nanoparticles, micelles, vesicles, liposomes, proteoliposomes, and/or virus like particles (VLP) that deliver each constituent as defined herein, complexed or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell.

Depending on their identity, the skilled person will know which type of formulation is the most appropriate for each constituent as defined herein. In a preferred embodiment, the invention provides a composition or a preparation which is in the form of a kit of parts comprising a L19 source as defined herein.

A medicine or medicament or pharmaceutical composition as defined herein may be locally or systemically administered. A medicament is preferably administered parenterally, e.g. by injection or infusion by intravenous, subcutaneous, intraperitoneal, intramuscular, intradermal, intraarterial or intralesional route. A preferred administration mode is subcutaneous or transdermal. An example of transdermal administration is a cream. The invention is not limited to a specific mode of administration of a medicament or a L19 source or a composition as defined herein. A preferred mode of administration is oral administration using a capsule or a tablet. Alternatively a medicament or a L19 source or a composition as defined herein may be locally administered via a catheter or a pump, or a suppository or a cream. Alternatively, a medicament or a L19 source or a composition as defined herein may be topically administered. The formulation of a medicament or a L19 source or a composition as defined herein depends on the intended mode of administration and (therapeutic) application. A pharmaceutical carrier can be any compatible, non toxic substance suitable to deliver said compound to a subject. E.g. sterile water, or inert solids or excipients may be used as the carrier, usually complemented with pharmaceutically acceptable adjuvants, buffering agents, dispersing agents, and the like. Compositions will either be in liquid, e.g. a stabilized suspension of said compound, or a composition comprising said compound, or in solid and/or dry forms: e.g. powder. For oral and rectal administration, said compound can be administered in solid dosage forms, such as capsules, tablets, suppositories, and powders, or in liquid dosage forms, such as elixirs, syrups, cream, ointment and suspensions. Another form may be a semi-solid or semi-liquid form wherein said compound is present as a liquid form in or on a solid support such as a patch.

A composition may be in the liquid, solid or semi-liquid or semi-solid form as already defined herein.

In a preferred embodiment, other compounds are used sequentially or simultaneously with a L19 source or a composition in order to improve the specificity of the therapeutic or prophylactic treatment. It is advantageous for example to use other compounds that will further enhance the anti-inflammatory response of the treated subject. More preferably, such compounds are not present in a single composition together with a L19 source or composition. Such compound may be an antibody, a DMARD (disease-modifying anti-rheumatic drugs), a NSAID (Non-steroidal Anti-inflammatory Agents) and/or an IL-10 inducer such as those described in table 1 of (13). An IL-10 inducer includes a compound selected from the group consisting of: cordycepin, a gold salt, a corticosteroid, cyclosporine A, ST1959

3-(2-ethylphenyl)-5-(3-methoxyphenyl)-1H-1,2,4-triazole, SR 31747A, SSR 125329A, aprotinin, linomide, monomethylfumarate, cAMP-elevating agents such as rolipram or cicaprost, a catecholamine, vitamin D3, a fish oil comprising a n-3 polyunsaturated fatty acid, an estriol sex hormone, KM 2210 or bestrabucil, a type I IFN such as IFN-τ, IFN-α or IFN-β, a mimic auto-antigen as glatiramer acetate (copolymer I), a pyrimidylpiperazine or a derivative thereof, 1-ethyl-3-(3-dimethyl aminopropyl) urea dihydrochloride, 5'-methylthioadenosine and a pirfenidone such as 5-methyl-1-phenyl-1H-pyridine-one.

Use

In a further aspect, there is provided the use of a L19 source or of a composition as defined herein for the manufacture of a medicament for preventing or treating an inflammatory disorder in an individual. Each feature of said use has earlier been defined herein.

A treatment in a use or in a method according to the invention is at least one week, at least one month, at least several months, at least one year, at least 2, 3, 4, 5, 6 years or more. Each L19 source as defined herein for use according to the invention may be suitable for direct in vivo, in vitro or ex vivo administration to a cell, tissue and/or an organ of individuals affected by or at risk of developing an inflammatory disorder, and may be administered directly in vivo to said individuals. The frequency of administration of a L19 source or composition of the invention may depend on several parameters such as the age of the patient, the number of molecules (i.e. dose), the formulation of said molecule. The frequency may be daily, weekly or ranged between at least once in two weeks, or three weeks or four weeks or five weeks or a longer time period.

Method

In a further aspect, there is provided a method for alleviating one or more symptom(s) of an inflammatory disorder in an individual, in a cell, tissue or organ of said individual or alleviate one or more characteristic(s) or symptom(s) of an individual or a cell, tissue or organ of said individual, the method comprising administering to said individual a L19 source or a composition as defined herein.

In one embodiment said method is performed in vitro, for instance using a cell culture or a tissue culture. Said method may also be ex vivo. Preferably, said method is in vivo. Each feature of these methods has already been defined herein. In a method of the invention, a L19 source may be combined with an additional compound known to be used for treating an inflammatory disorder in an individual. Such compound may be an antibody, a DMARD (disease-modifying anti-rheumatic drugs), a NSAID (Non-steroidal Anti-inflammatory Agents) and/or an IL-10 inducer as described in (13). Preferred IL-10 inducers have already been identified earlier herein.

Definitions

Nucleic Acid Molecule

A nucleic acid molecule may be a cDNA or synthetic DNA. The DNA may be double-stranded or single-stranded and if single-stranded may be the coding strand or non-coding (anti-sense) strand. DNA or RNA with a backbone modified for stability or for other reasons are a further part of the invention. A nucleic acid molecule is represented by a nucleotide sequence. A nucleotide sequence may be an allelic variant of the nucleotide sequence according to the invention. If desired, the nucleotide sequence can be prepared or altered synthetically so the known codon preferences of the intended expression host can advantageously be used. Depending on the size of the nucleic acid molecule, it could be identify as being an oligonucleotide. An oligonucleotide may comprise at least 10, 20, 30, 40, 50, 60, 70, 80, 90, 100 nucleotides.

Polypeptide

"Polypeptide" as used herein refers to any peptide, oligopeptide, polypeptide, gene product, expression product, or protein. A polypeptide is represented by an amino acid sequence. It may comprise from 2 to 267 (i.e. length of SEQ ID NO:1, 5, 7, 9, 11, 13, 15, 17, 19, 21, 23, 25, 27 or 29) or 5 to 265 or 8 to 260 or 10 to 250 amino acids. It may comprise more than 267 amino acids. The term "polypeptide" encompasses naturally occurring or synthetic molecules. An oligopeptide may comprise 2 to 20 amino acids. A peptide may comprise 5 to 10 or 5 to 20 or 5 to 30 or 5 to 50 amino acids.

Identity/Similarity

"Sequence identity" is herein defined as a relationship between two or more amino acid (polypeptide or protein or peptide or protein fragment) sequences or two or more nucleic acid (polynucleotide, nucleic acid or nucleotide or oligonucleotide) sequences, as determined by comparing the sequences. In a preferred embodiment, sequence identity is calculated based on the full length of two given SEQ ID NO or on part thereof. Part thereof preferably means at least 50%, 60%, 70%, 80%, 90%, or 100% of both SEQ ID NO. In the art, "identity" also means the degree of sequence relatedness between amino acid or nucleic acid sequences, as the case may be, as determined by the match between strings of such sequences.

"Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; H is to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridization Conditions

Hybridization conditions for a nucleic acid molecule may have low or medium or high stringency (southern blotting procedures). Low or medium or high stringency conditions means pre-hybridization and hybridization at 42° C. in 5×SSPE, 0.3% SDS, 200 pg/ml sheared and denatured salmon sperm DNA, and either 25% or 35% or 50% formamide for low or medium or high stringencies respectively. Subsequently, the hybridization reaction is washed three times for 30 minutes each using 2×SSC, 0.2% SDS and either 55° C. or 65° C., or 75° C. for low or medium or high stringencies respectively.

Nucleic Acid Construct/Expression/Control Sequences

A nucleic acid construct comprises a nucleotide sequence encoding a protein or a protein fragment as defined herein. A nucleic acid construct comprising a nucleic acid molecule coding for a given protein or protein fragment as defined herein will ensure expression of the given nucleic acid molecule, and of the corresponding protein or protein fragment in a treated subject. In a more preferred embodiment, a nucleic acid construct comprises more than one nucleic acid molecule, each nucleic acid molecule coding for a given protein or protein fragment. In an even more preferred embodiment, a nucleic acid construct comprises two, three, four nucleic acid molecules, each nucleic acid molecule coding for a given protein or protein fragment. In a preferred embodiment, a nucleic acid construct comprises an expression cassette, said expression cassette comprising each needed nucleic acid molecule. Each nucleic acid molecule is operably linked with other nucleic acid molecule present. Most preferably, a suitable promoter is operably linked with the expression cassette to ensure expression of the nucleic acid molecule in a subject.

"Operably linked" is defined herein as a configuration in which a control sequence is appropriately placed at a position relative to the nucleotide sequence coding for the polypeptide of the invention such that the control sequence directs the production/expression of the polypeptide of the invention in a cell and/or in a subject.

Expression will be understood to include any step involved in the production of the polypeptide including, but not limited to transcription, post-transcriptional modification, translation, post-translational modification and secretion.

Control sequence is defined herein to include all components, which are necessary or advantageous for the expression of a polypeptide. At a minimum, the control sequences include a promoter and transcriptional and translational stop signals. Optionally, a promoter represented by a nucleotide sequence present in a nucleic acid construct is operably linked to another nucleotide sequence encoding a nucleic acid molecule as identified herein.

An expression vector may be any vector which can be conveniently subjected to recombinant DNA procedures and can bring about the expression of a nucleotide sequence encoding a polypeptide of the invention in a cell and/or in a subject. As used herein, the term "promoter" refers to a nucleic acid fragment that functions to control the transcription of one or more genes or nucleic acids, located upstream with respect to the direction of transcription of the transcription initiation site of the gene, and is related to the binding site identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter. Within the context of the invention, a promoter preferably ends at nucleotide −1 of the transcription start site (TSS).

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a L19 source or a composition as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

BRIEF DESCRIPTION OF THE DRAWINGS

FIG. 7. LmL19 peptide IL-10 production. Cells were obtained and cultures as indicated in the text. The level of IL-10 in culture supernatants were analyzed by ELISA.

The assay has been performed once using pooled cells obtained from three naive mice (Assayed by duplicate). *P<0.05 when each group was compared with the non-stimulated cells.

EXAMPLES

Example 1

Cloning and Expression.

The gene was characterized after in silico search in the *L. major* genome database. On the basis of the sequence two oligonucleotides were synthesized (see below) and employed as primer for a PCR using DNA extracted from *L. major* [clone V1 (MHOM/IL/80(Friedlin)] parasites. The obtained DNA was digested with BamHI/HindIII, cloned in the corresponding sites of pBluescript plasmid and sequenced. The obtained DNA sequence and the deduced aminoacid sequence is shown below, respectively.

A. Oligonucleotides employed.

```
LmL19D:
                                        (SEQ ID NO: 3)
cgGGATCCATGACCCCTCTCTCCCTCTC
(Underlined a BamHI cut site was included
for cloning purposes).

LmL19R:
                                        (SEQ ID NO: 4)
cccAAGCTTTTACTTCTTCGACTTCTTCAC
(Underlined a HindIII cut site was included
for cloning purposes).
```

B. Nucleotide sequence. (The restriction enzymes cut sites are included and marked in italics and underlined: these sites do not belong to the nucleic acid molecule encoding L19 from *Leishmania major* or Lm)

Sequence Analysis of the LmL19 (SEQ ID NO:2 is the Sequence Below without the Underlined Sequence Added for Cloning Purposes)

```
GGATCCATGA CCCCTCTCTC CCTCTCTTCC TCCCGCCACA

GTTTTAAGCA GAACGAAACG CAGAACATGG TGTCTCTGAA

GCTGCAGGCT CGCCTTGCGT CGAGCATCCT CGGCTGCGGC

CGCGCCCGCG TGTGGCTGGA CCCCAACGAG GCGGTGGAGA

TCCAGAACGC GAACTCGCGC AAGAGCGTGC GCAAGCTGAT

CAAGGATGGC TTCATCATCC GCAAGCCGGT GAAGGTGCAC

TCGCGCGCGC GGTGGCGTAA AATGAAGGAG GCGAAGGACA

TGGGGCGCCA CAACGGCGTT GGGCGCCGCG AGGGTAGCCG

CGAGGCCCGC ATGCCGAGCA AGGAGTTGTG GATGCGCCGC

CTGCGCATTC TGCGCCGCCT GCTGCGCAAG TACCGCGCGG

ACAAGAAGAT TGACCGCCAC GTGTACCGCG ACCTGTACAT

GCGCGCGAAG GGTAACGTGT TCCGCAACAA GCGCAACCTT

GTGGAGCACA TCCACAAGAT CAAGAATGAG AAGAAGAAGG

AGCGCCAGCT GGCGGAGCAG CTCGCGGCGA AGCACCTGCG

CGACGAGCAG AACCGCAACA AGGCTCGCAA GCAGGAGCTG

AAGAAGCGCG AGAAGGAGCG CGAGCGCGCG AGGCGCGACG

ACGCTGCTGC CGCTGCGCAG AAGAAGAAGG CGGACGCCGC

GAAGAAGTCC GCCGCGCCTG CTGCGAAGTC CGCCGCGCCT

GCCGCGAAGG CTGCTGCCCC CGCCACGAAG GCCGCTGCTG

CTGCCCCCGC CACGAAGGGT GCTGCGCCGG TGAAGAAGTC

GAAGAAGTAA AAGCTT
```

C. Deduced amino acid sequence (SEQ ID NO:1)

```
MTPLSLSSSR HSFKQNETQN MVSLKLQARL ASSILGCGRA

RVWLDPNEAV EIQNANSRKS VRKLIKDGFI IRKPVKVHSR

ARWRKMKEAK DMGRHNGVGR REGSREARMP SKELWMRRLR

ILRRLLRKYR ADKKIDRHVY RDLYMRAKGN VFRNKRNLVE

HIHKIKNEKK KERQLAEQLA AKHLRDEQNR NKARKQELKK

REKERERARR DDAAAAAQKK KADAAKKSAA PAAKSAAPAA

KAAAPATKAA AAAPATKGAA PVKKSKK*
```

The DNA encoding LmL19 was subcloned in the BamHI/HindIII sites of the pQE-30 prokaryotic expression plasmid that allow the obtention of the recombinant protein fused to 6xhistidines.

Figure 1:
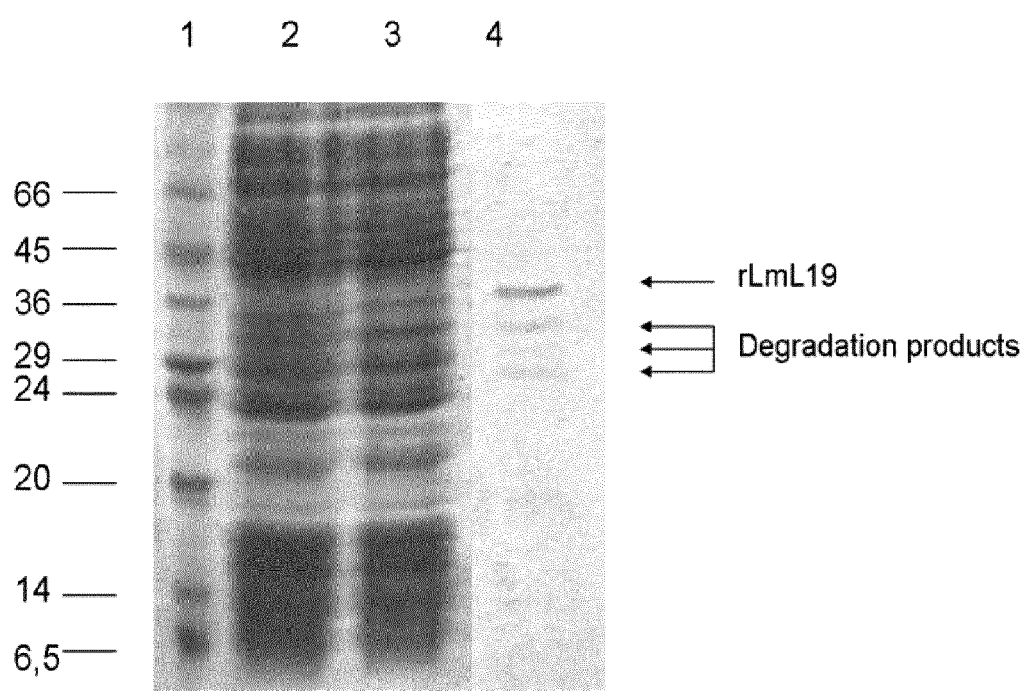
FIG. 1. Purification of the his-LmL19. SDS-PAGE gel showing the different steps in the purification of the rLmL19 protein. (1) Molecular weight standard. Total bacterial extracts after (2) and before (3) column passage. (4) Purified protein.

*Escherichia coli* (strain M15) cultures transformed with the recombinant plasmid was employed for the expression of the recombinant protein. The first assays were done at 37° C., but we observed that the protein was degraded inside the bacteria. For that reason, cultures were induced at 30° C. in order to decrease protein degradation. At these conditions we observed a low production of the intact recombinant protein. Thus, rLmL19 was purified by affinity chromatography under denaturing conditions. The purified protein obtained presents some degradation bands with lower molecular weight (FIG. 1). The recombinant proteins were passed through a polymyxin-agarose column to remove endotoxins.

Stimulation of Mice Spleen Cells with the Recombinant rLmL19.

Figure 2A:
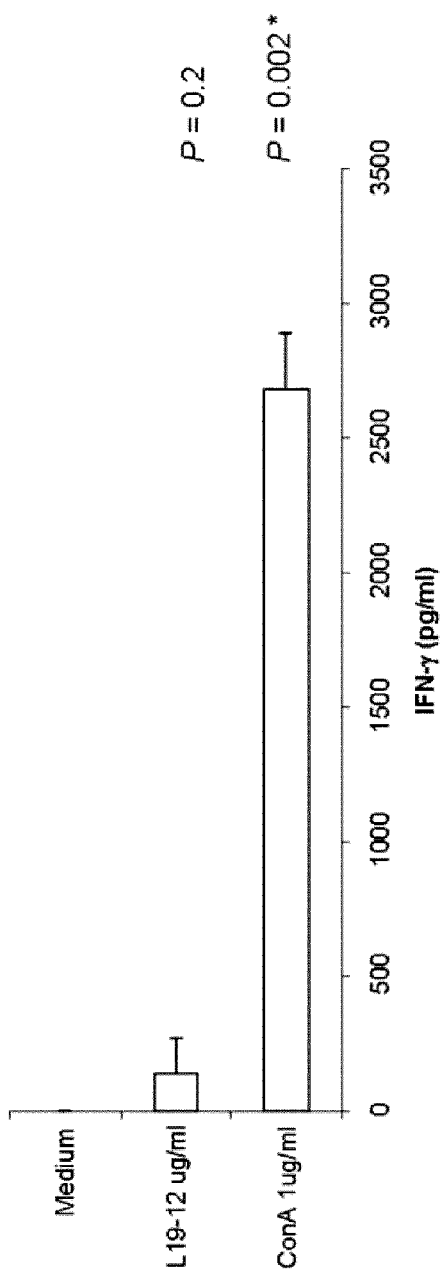
FIG. 2. IFN-gamma and IL-10 production by splenocytes of naive BALB/c mice (n=6) stimulated in vitro with LmL19. The P value obtained after the statistical analysis performed by a Student's t-test is shown. Differences in the production of the cytokines between the LmL19 or the Concanavalin A (ConA) stimulated cells were considered significant when P<0.05*).
Figure 2B:
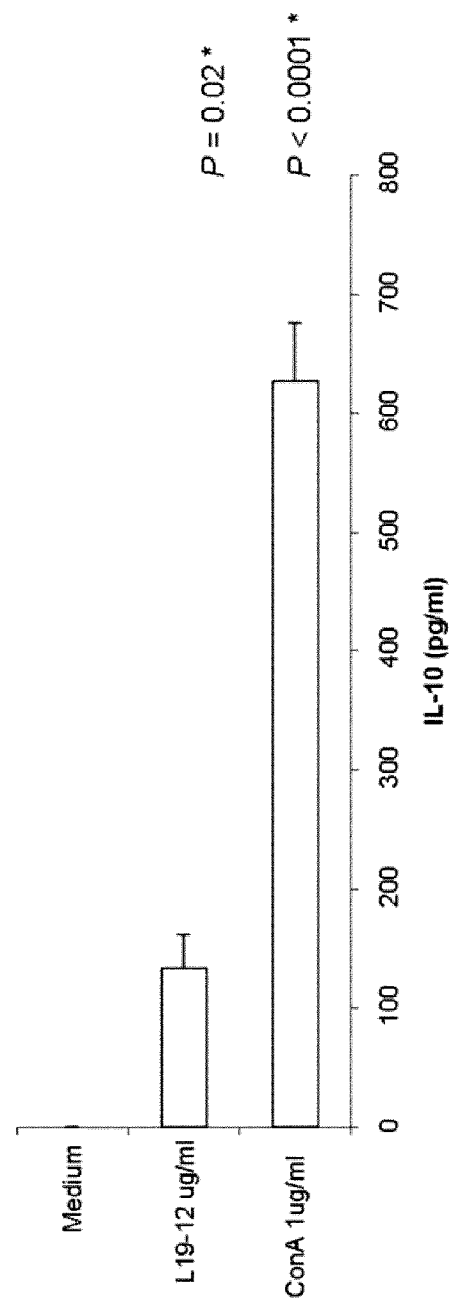

Single-cell preparations from spleen tissue were plated in duplicate in 24-well plates at $5 \times 10^6$ cells/ml. Cells were incubated in complete RPMI medium supplemented with 2 mM L-glutamine, penicillin (100 U/ml), streptomycin (100 µg/ml) and 10% heat inactivated foetal bovine sera alone (background control; medium) or stimulated with rLmL19 (12 ug/ml) or ConA (1 ug/ml) at 37° C. in 5% CO2 for 72 h. IFN-gamma and IL-10 release in the culture supernatants was assessed by sandwich ELISA (FIG. 2). It can be concluded that the recombinant LmL19 protein induced an specific production of IL-10, without the production of IFN-gamma by spleen cells obtained from naive mice.

Stimulation of Human Peripheral Mononuclear Blood Cells (PBMCs) from Humans with the Recombinant rLmL19.

Figure 3A:
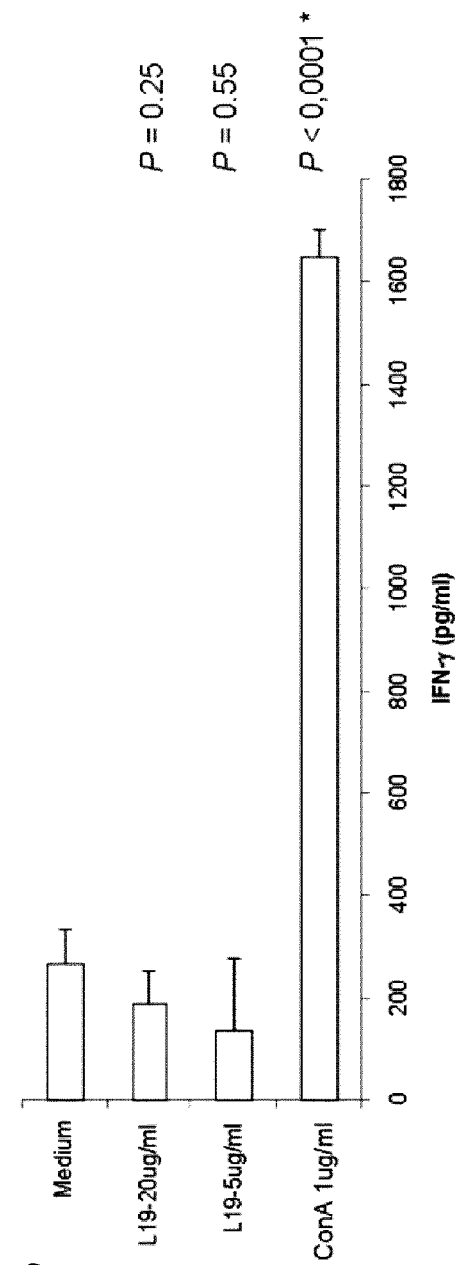
FIG. 3. IFN-gamma and IL-10 production by PBMCa of healthy human donorse (n=3) stimulated in vitro with LmL19. The P value obtained after the statistical analysis performed by a Student's t-test is shown. Differences in the production of the cytokines between the LmL19 or the ConA stimulated cells were considered significant when P<0.05*).
Figure 3B:
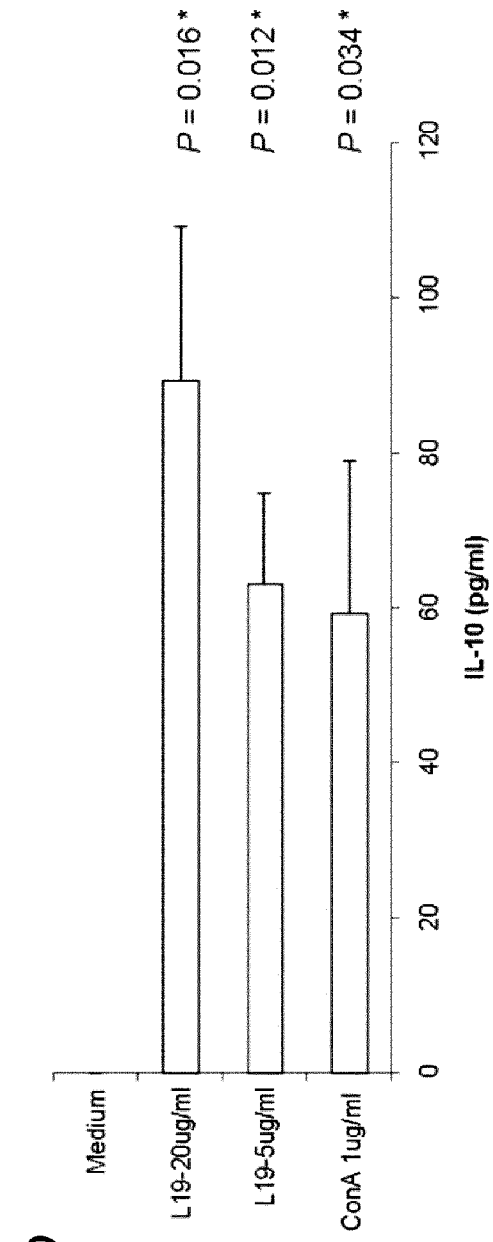

PBMC were obtained from heparinized venous blood by passage over a Ficoll Hypaque gradient. PBMC were washed three times and resuspended at a concentration of $5 \times 10^6$ cells/ml in RPMI supplemented with 2 mM L-glutamine, penicillin (100 U/ml), streptomycin (100 µg/ml) (Gibco, N.Y.) and 10% heat inactivated human AB serum). Cells were plated in 24 well tissue culture plates at a concentration of $5 \times 10^6$ cells/ml and incubated at 37° C., 5% CO2. Stimulation was performed by addition of rLmL19 (20 µg/ml and 5 ug/ml) and ConA (1 ug/ml) for 72 h. As above, IFN-gamma and IL-10 release in the culture supernatants was assessed by sandwich ELISA (FIG. 3).

As occurred with mice spleen cells, PBMC form healthy human donors produced IL-10 after in vitro stimulation with the recombinant LmL19. The production of this cytokine was dose dependent.

Expression of the rLmL19 as a Fusion Protein with the Maltose Binding Protein.

These preliminary results were indicating that the rLmL19 protein was able to induce the IL-10 release from human and mice white cells. The level of production of the recombinant protein was not yet optimal.

Figure 4:
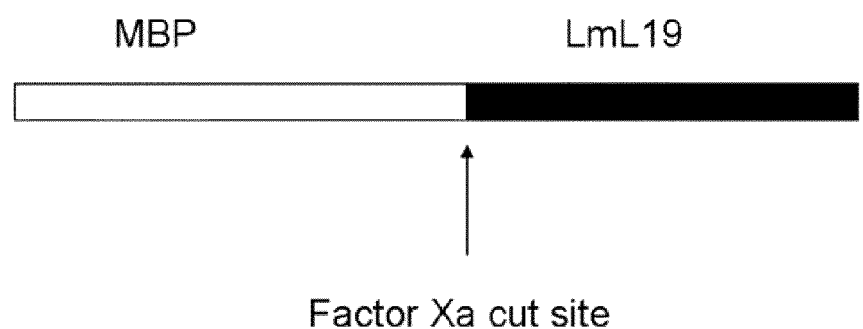
FIG. 4. Schematic representation of the MBP-LmL19 recombinant protein.

In order to improve protein production the DNA encoding the LmL9 protein was cloned in the pMal-c2 prokaryotic expression vector. This vector allows the production of heterologous proteins in *E. coli* fused to the bacterial MBP protein. As indicated in FIG. 4 the fusion protein and the heterologous protein can be separated using an specific protease (Xa factor) due to the presence of an Xa factor cut site between both proteins.

*E. coli* (strain XL1-blue) cultures transformed with the recombinant plasmid was employed for the expression of the recombinant protein. Protein was overexpressed as a soluble product that was purified by affinity chromatography under native conditions in amilose columns. Using this system higher level of recombinant protein was obtained (not shown).

Example 2: Skin Study

The objective of this study was to evaluate the anti-inflammatory capacity of a protein named, L19, in human skin explants. This was done by a screening method to study the protective efficacy of this protein versus radiation of ultraviolet (UV) light on the skin.

The basis of this work is the performance of a single inflammatory study on skin explants to assess the anti-inflammatory capacity of said product versus radiation with UV light. The study was divided into the following tasks in order to achieve the proposed objective.

Basic Cytotoxicity Screening

A single assay was performed using the MTT technique to determine the maximum concentration of the product to be assayed in efficacy screening. This is a colorimetric assay based on the metabolic reduction of tetrazolium salts (MTT) due to cell metabolism (cellular respiration) of mouse fibroblasts (BALB/3T3. This metabolic reduction of the MTT is caused by the mitochondrial enzyme succinate dehydrogenase, which produces a blue compound (formazan) and determines the mitochondrial functionality of the treated cells. The number of live cells is proportional to the resulting blue color. The product was incubated at 8 different concentrations (6 replicas of each concentration) for 24 hours.

Anti-Inflammatory Efficacy Screening

Efficacy was assessed by an anti-inflammatory study consisting in a single assay on skin explants that analyzed two interleukins present in the inflammation caused by UV radiation using the ELISA technique.

The study groups were as follows:
  Healthy control group. 3 skin explants. These did not receive UV light radiation.
  Damaged group. 3 skin explants irradiated with UV light.
  Test group. 9 skin explants irradiated with UV light and then incubated with recombinant Lm L19 (SEQ ID NO:1) expressed in *E. Coli*.
  Test group 2. 9 skin explants not irradiated and then incubated with Lm L19 (SEQ ID NO:1) expressed in *E. coli*.

Three different product concentrations, 3 replicas per concentration (the highest product concentration was determined by product toxicity screening).

After irradiation of the explants with ultraviolet light, Lm L19 (i.e. SEQ ID NO:1) expressed in *E. Coli* was incubated; 24 hours later, we measured two interleukins involved in the inflammatory effect caused by ultraviolet light on the skin, IL-10 and TNFα.

Materials and Method

Cell Cultures

As the experimental system for cytotoxicity screening, the study used a cell culture of the immortalized line of mouse fibroblasts from the cell line BALB/3T3 from the European Collection of Cell Cultures (ECACC) Cat. No. 86110401.

The immortalized fibroblasts from the ECACC grew in a DMEM medium with 10% FCS (Fetal Calf Serum). After thawing, the cells were cultivated in a monolayer in a humid atmosphere with 5% $CO_2$ and at a temperature of 37° C. During this time, the culture medium was changed every 2-3 days, according to the instructions of the supplier. After this period, when the culture flasks reached a confluence of 80%, the cells were distributed on 96-well plates at a concentration of 5,000 cells per well.

Cytotoxicity Study with Endpoint, MTT

During the cytotoxicity assay, the cells were treated with different concentrations of the study product known as L19. After 24 hours of treatment, MTT staining was performed. This assay is based on the metabolic reduction of 3-(4,5-dimethyl thiazole-2-yl)-2,5-diphenyl tetrazol bromide (MTT) or tetrazolium salts (yellow and soluble) produced by the mitochondrial enzyme succinate-dehydrogenase that generates a compound with a blue color (formazan) that allows determination of the mitochondrial functionality of the treated cells. This method is widely used to measure cell survival and proliferation. The number of live cells is proportional to the amount of formazan produced. Since dead cells do not breath, they do not present the enzyme and therefore cannot reduce it since they do not present succinate-dehydrogenase. The greater the reduction in MTT, the bluer the color and the greater cell viability.

The experiment was performed on 96-well plates with 3T3 cells grown on a monolayer with 80% confluence. These cytotoxicity studies allowed us to determine LC80, LC50 and LC20 values (product concentrations that reduce cell viability by 80%, 50% and 20%, respectively).

During this task, a plate of immortalized fibroblasts was incubated with eight distinct concentrations of L19 protein for 24 hours (1 product plate with 6 replicas per concentration assayed) and a second MTT assay control plate with sodium dodecyl sulfate (SDS) at eight distinct concentrations (1 plate with MTT, with 6 replicas per concentration assayed) as the toxicity reference product. This was used to establish a standard curve for cell death. All the study plates were also seeded with fibroblasts in at least 12 wells that were used as healthy controls, and 3T3 cultures with only the culture medium, where L19 was not added to the study plate nor SDS to the cell death control plate (SDS Data: LC20: 0.124 mg/ml; LC50: 0.142 mg/ml; LC80: 0.163 mg/ml).

According to the concentration of protein L19 supplied by LETI, the highest concentration assayed was 200 µg/ml at dilutions of 1:2. The final concentrations used are detailed below: C2: C3: C4: C5:C6:C8:1.56 µg/ml.

After incubation, the plates were developed with MTT and absorbance was measured at 540 nm with an ELISA plate reader. The results obtained were used to calculate the lethal concentration values LC80, LC50 and LC20, in the fibroblast cultures for the products under study.

Interleukin-10 and TNFα Determination Assay

The interleukin-10 and TNFα quantitation assay was performed with the supernatant of the skin explant culture mediums. Quantitative determination of both IL-10 and TNFα was performed with BD OptEIA™ ELISA kits manufactured by Becton Drive, Franklin Lakes, N.J., USA):
Human TNF ELISA Kit II
L19 efficacy was assessed by quantitation of the interleukins induced by UV radiation on human skin explants.
Exposure to Solar Simulator Light:

The plate with the skin samples was exposed to UV/vis light emitted by a SOL 500 (Dr. Hönle) solar simulator. Light intensity was measured throughout the exposure process by a UV light meter. Radiation doses can be adjusted with these values, considering that during 5 minutes of exposure, the cells receive approximately 1 J/cm$^2$ at that intensity. The final time of exposure of the skin explants was 50 minutes, implying radiation of 10 J/cm$^2$.

The groups included in the study were:
Healthy control group. 3 skin explants. These did not receive UV light radiation.
Damage group. 3 skin explants irradiated with UV light.
Test group. 9 skin explants irradiated with UV light and then incubated with recombinant LmL19 (i.e. SEQ ID NO:1) expressed in *E. coli*.
Test group 2. 9 skin explants not irradiated and then incubated with LmL19 (i.e. SEQ ID NO:1).

Three different product concentrations, 3 replicas per concentration (the highest product concentration was determined by product toxicity screening). After irradiation of the explants with ultraviolet light (10 J/cm$^2$) they were incubated with product L19. After 24 hours, we measured two interleukins involved in the inflammatory effect caused by ultraviolet light on skin, IL-10 and TNFα.

IL-10 and TNFα were quantified by adding 100 µl of each of the IL-10 and TNFα standards included in the kits manufactured by BD Biosciences (BD OptEIA™ ELISA Sets: IL-10 Cat-No. 555157 and TNF Cat. No. 555212), as well as 100 µl of the culture medium used to incubate each of the samples, all in duplicate and incubating on ELISA plates at ambient temperature for 2 hours. The wells were then washed with PBS, 200 µl of the conjugated solution was added and incubation was performed for 1 hour. The wells were then washed again, 200 µl of the substrate solution was added and incubation was performed for 20 minutes at ambient temperature. Lastly, 50 µl of the stopper solution was added and absorbance was read at 450 nm with a reference of 540 nm. The absorbance results were extrapolated to the amount of IL-10 and TNFα, using the curve obtained with the standards of both cytokines as reference.

Results and Discussion
Basic Cytotoxicity Screening
Cytotoxicity Study of Protein L19.

To determine the maximum concentration of the study product in efficacy screening, a single assay was performed using the MTT technique on an immortalized line of fibroblasts, BALB/3T3, which were seeded on 96-well plates with an approximate density of 5,000 cells per well. The product was incubated at 8 different concentrations (6 replicas of each concentration) for 24 hours.

The results of this assay were used to define the concentrations necessary to determine $LC_{80}$, $LC_{50}$ and $LC_{20}$. LC is the lethal concentration of the substance. $LC_{80}$ is the concentration of the substance at which 80% of the cell population dies, $LC_{50}$ is the concentration of the substance at which 50% of the cell population dies and $LC_{20}$ is the toxic concentration of the substance at which 20% of the cell culture population dies.

In these assays, each fibroblast plate was incubated with six distinct active concentrations for 24 hours:
C2: C3: C4: C5:C6:C8:1.56 µg/Ml.

After incubation, the plates were developed for analysis with MTT and absorbance was measured at 540 nm with an ELISA plate reader. The following table shows LC80, LC50 and LC20, obtained for each product (Table 1) without statistical significance:

TABLE 1

Results for LC20, LC50 and LC80 of protein L19 from LETI obtained by cytotoxicity assays, MTT.

| | | |
|---|---|---|
| 485.83934 | 228.357 | 22.03021 |

The values are expressed as mean (µg/ml)

The results of this cytotoxicity assay were obtained taking into consideration the absorbance values obtained in the healthy control cultures that were not incubated with the L19 product, as a reference of 100% viability. As well as occurred with the cell death values, viability was 0% with the SDS product at a concentration >175 μg/ml (SDS Data: LC20: 0.124 mg/ml; LC50: 0.142 mg/ml; LC80: 0.163 mg/ml).

Due to the results obtained in the cytotoxicity assay, it was decided that for the next task, anti-inflammatory efficacy screening of protein L19, the highest concentration to test of the product would be 25 μg/ml, as well as 12.5 μg/ml and 6.25 μg/ml.

The choice of the highest concentration, 25 μg/ml, refers to LC20. This value is adequate for the assay of the product on skin since it is at the minimum toxicity limit for the product. It should also be noted that toxicity screening was performed in a single culture of fibroblasts. Monocultures are always more sensitive to the toxicity of a product than an organotypic culture such as skin explant.

Anti-Inflammatory Efficacy Screening

Study on the Anti-Inflammatory Capacity of Protein L19 after Irradiation of UV Light on Human Skin Explants.

Treatment of human skin explants with protein L19 (25 μg/ml, 12.5 and 6.25 μg/ml for 24 hours) (Lm L19 or SEQ ID NO:1) was performed to study the anti-inflammatory effect of the protein. The study groups were divided into explants that were irradiated with UV light and later incubated with protein L19 and explants that were exposed to the product but not irradiated with UV light.

The study was performed on organotypic cultures of human skin explants from cosmetic surgery. The assay used two control groups; culture without protein L19 or solar radiation and a damage control group, culture without the protein but irradiated with solar light. The concentrations and conditions can be found below:

Control Group: Skin explants in normal culture conditions.
L19-25 μg/ml Group; Skin explants incubated with 25 μg/ml of protein for 24 hours.
L19-12.5 μg/ml Group; Skin explants incubated with 12.5 μg/ml of protein for 24 hours.
L19-6.25 μg/ml Group; Skin explants incubated with 6.25 μg/ml of protein for 24 hours.
Control/UV Group: Skin explants in normal culture conditions and irradiated with UV light, 10 J/cm$^2$.
L19-25 μg/ml/UV Group; Skin explants irradiated with UV light (10 J/cm$^2$) and then incubated with 25 μg/ml of protein for 24 hours.
L19-12.5 μg/ml/UV Group; Skin explants irradiated with UV light (10 J/cm$^2$) and then incubated with 12.5 μg/ml of protein for 24 hours.
L19-6.25 μg/ml/UV Group; Skin explants irradiated with UV light (10 J/cm$^2$) and then incubated with 6.25 μg/ml of protein for 24 hours.

At the end of the incubation period (24 hours) quantification was performed on both cytokines, IL-10 and TNFα, with the ELISA technique to determine the quantity of these cytokines. A single assay was performed in this task, where protein L19 from LETI Laboratories was analyzed. This assay used 3 replicas of each condition and each replica was analyzed by ELISA technique in duplicate.

Figure 5:
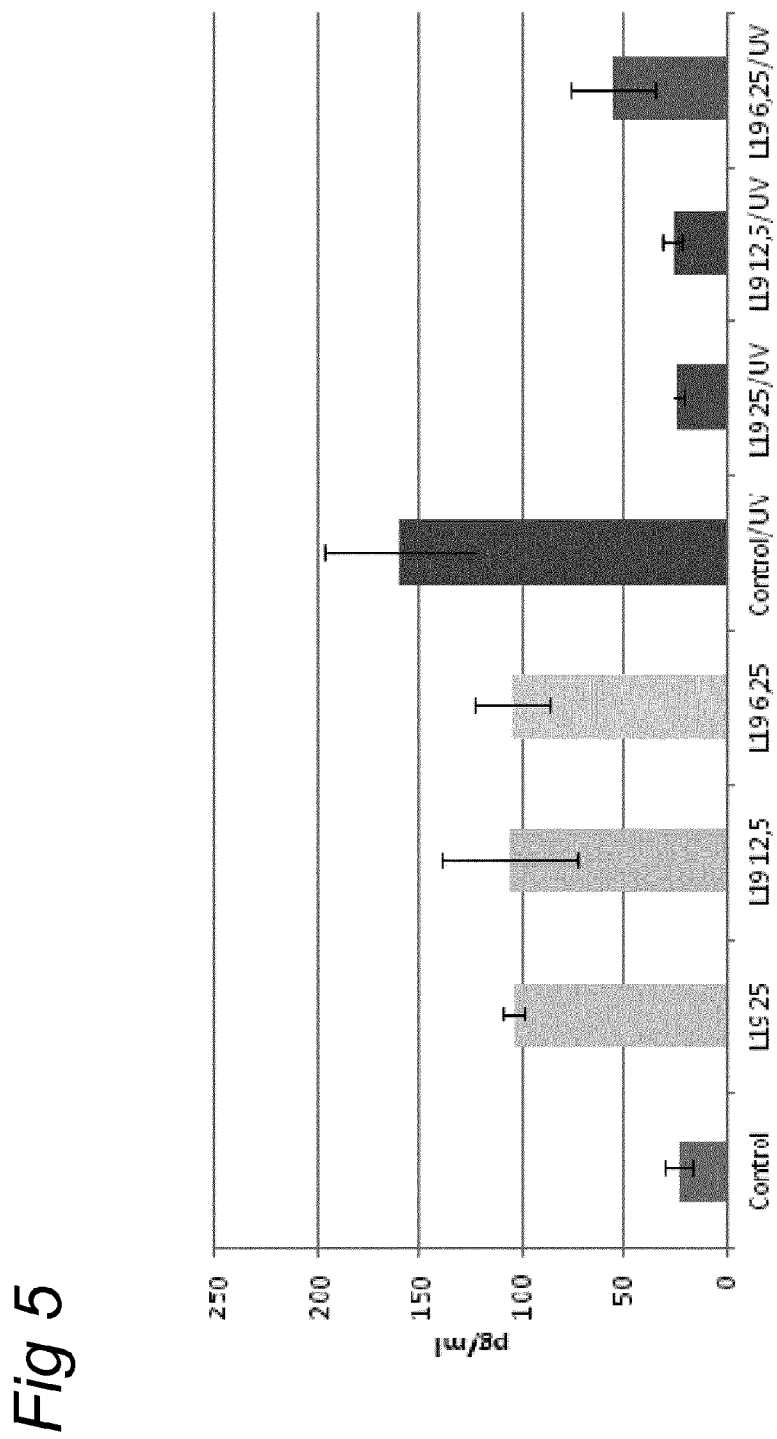
FIG. 5. Concentration of TNFα in the different study groups after 24 hours of incubation (pg/ml). The values are presented as average±standard deviation. #; p<0.005, test groups without irradiation compared to the Control group.*; p<0.005, irradiated test groups compared to the Control/UV Group.

The concentration of TNFα (FIG. 5) and the concentration of IL-10 (FIG. 6) for these study groups are shown below, both for skin explants irradiated with UV light and those that were not irradiated. FIG. 5 shows the production of TNFα in the skin explants in the conditions to which they were submitted.

The inflammatory reaction produced by UV radiation in the Control/UV group (153.9±44 pg/ml) is significantly higher than in the control group without radiation (22.9±7.3 pg/ml). This indicates that radiation with 10 J/cm$^2$ of UV light (in monoculture, the radiation used is normally 1 J/cm$^2$) on skin explants triggers an inflammatory reaction in this case. This reaction is sufficient to see whether protein L19 has anti-inflammatory effects after incubation in skin samples exposed to this level of radiation.

As shown in the graph, the statistical study of this protein shows that the production of TNFα after UV light radiation decreases significantly in the explants that were incubated afterwards (for 24 hours) with protein L19 at concentrations of 25 and 12.5 μg/ml (23.3±2.8 and 25.9±4.8 pg/ml, respectively). The L19-6.25 μg/ml/UV group showed a non-significant reduction in the production of said cytokine.

On the other hand, the graph also shows a significant increase in the production of TNFα in the L19-25 μg/ml, L19-12.5 μg/ml and L19-6.25 μg/ml groups (that were not irradiated) in comparison with the Control group. All of the above leads us to consider that protein L19 could affect the skin in some way, generating an inflammatory reaction. This last point should be corroborated by further studies.

The significant decrease in the production of TNFα in the cultures with protein L19 treated afterwards with solar radiation versus the Control/UV group leads us to think that this protein may have an anti-inflammatory effect.

Figure 6:
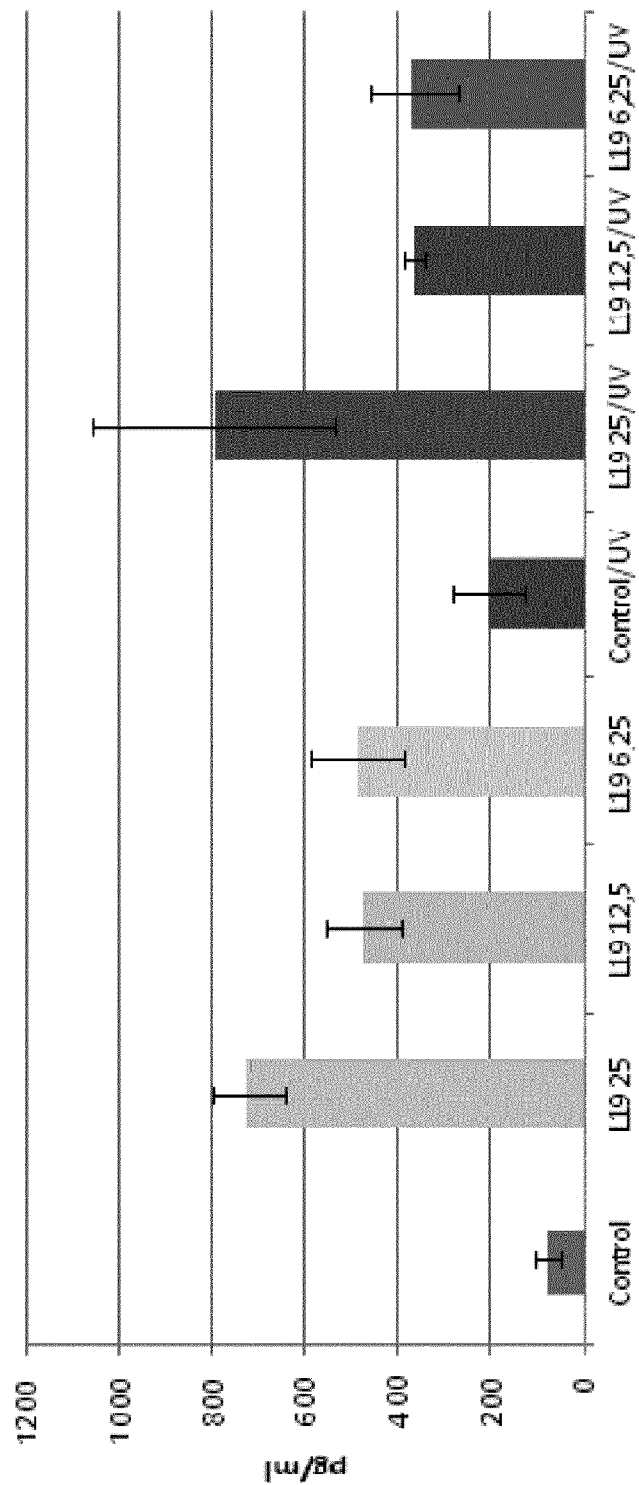
FIG. 6. Concentration of IL-10 in the different study groups after 24 hours of incubation (pg/ml). The values are presented as average±standard deviation. #; p<0.005, test groups without irradiation compared to the Control group. *; p<0.005, irradiated test groups compared to the Control/UV Group.

FIG. 6 shows the production of IL-10 in the skin explants in the conditions to which they were submitted. The analysis of IL-10 in both irradiated and non-irradiated groups incubated with protein L19 indicated a significant increase in the production of IL-10 at all the concentrations of the protein under study versus the non-irradiated Control group (#; p<0.005)

In the statistical study, this increase was observed to a lesser degree versus the Control group irradiated with UV light, where only the L19-12.5 μg/ml/UV group presents a significant increase (*; p<0.005), 363.7±22 pg/ml, versus the Control/UV group (203.1±77). This is due to the standard deviations in the other two study groups, L19-6.25 μg/ml/UV and L19-25 μg/ml/UV (366±94 and 724.8±288 pg/ml), that cause the statistical study to determine differences higher than a statistical significance of 0.005. An increase in the number of replicas would improve the statistical significance.

The data obtained indicate an increase in the production of IL-10, an anti-inflammatory cytokine, which corroborates the results obtained for TNFα, leading to the possibility that protein L19 triggers an anti-inflammatory cascade in skin explants, with an increased production of IL-10.

Conclusions

In the cytotoxicity study, toxicity of protein L19 was very low under values of 25 μg/ml. The choice of 25, 12.5 and 6.25 μg/ml to perform task 2 was based on cytotoxicity screening UV light radiation at 10 J/cm$^2$ produces a significant inflammatory effect in skin explant samples not incubated with protein L19 and significantly increases both TNFα levels and IL-10 levels (intrinsic anti-inflammatory reaction in skin).

Protein L19 causes a detectable reduction in the production of TNFα cytokine in the skin samples irradiated with UV light.

Protein L19 produces a general increase in IL-10 levels in all the groups incubated with the protein, both as regards samples that undergo UV light radiation and those that do not.

According to the results obtained, the capacity of protein L19 to activate an anti-inflammatory effect is very high.

Example 3: IL-10 Mediated Production of LmL19 and LmL19 Derived Peptides

Objective of the Study

To determine which regions of L19 (linear epitopes) are capable to induce the production of 1'-10 in spleen cultures.

Material

Twenty four different peptides were designed and synthesized chemically. Each of them corresponds to a linear region of the *Leishmania major* protein L19 (i.e. SEQ ID NO:1). Each peptides comprises 20 amino acids derived from *Leishmania major* L19 (i.e. SEQ ID NO:1), except peptide 24 which only comprises 14 amino acids. Each peptide overlaps 9 amino acids with the previous peptide.

```
1: Peptide 1:
                                   (SEQ ID NO: 31)
MTPLSLSSSRHSFKQNETQN 2: Peptide 2:
                                   (SEQ ID NO: 32)
SFKQNETQNMVSLKLQARLA 3: Peptide 3:
                                   (SEQ ID NO: 33)
SLKLQARLASSILGCGRARV 4: Peptide 4:
                                   (SEQ ID NO: 34)
ILGCGRARVWLDPNEAVEIQ 5: Peptide 5:
                                   (SEQ ID NO: 35)
DPNEAVEIQNANSRKSVRKL 6: Peptide 6:
                                   (SEQ ID NO: 36)
NSRKSVRKLIKDGFIIRKPV 7: Peptide 7:
                                   (SEQ ID NO: 37)
DGFIIRKPVKVHSRARWRKM 8: Peptide 8:
                                   (SEQ ID NO: 38)
HSRARWRKMKEAKDMGRHNG 9: Peptide 9:
                                   (SEQ ID NO: 39)
AKDMGRHNGVGRREGSREAR 10: Peptide 10:
                                   (SEQ ID NO: 40)
RREGSREARMPSKELWMRRL 11: Peptide 11:
                                   (SEQ ID NO: 41)
SKELWMRRLRILRRLLRKYR 12: Peptide 12:
                                   (SEQ ID NO: 42)
LRRLLRKYRADKKIDRHVYR 13: Peptide 13:
                                   (SEQ ID NO: 43)
KKIDRHVYRDLYMRAKGNVF 14: Peptide 14:
                                   (SEQ ID NO: 44)
YMRAKGNVFRNKRNLVEHIH 15: Peptide 15:
                                   (SEQ ID NO: 45)
KRNLVEHIHKIKNEKKKERQ
```

-continued

```
16: Peptide 16:
                                   (SEQ ID NO: 46)
KNEKKKERQLAEQLAAKHLR 17: Peptide 17:
                                   (SEQ ID NO: 47)
EQLAAKHLRDEQNRNKARKQ 18: Peptide 18:
                                   (SEQ ID NO: 48)
QNRNKARKQELKKREKERER 19: Peptide 19:
                                   (SEQ ID NO: 49)
KKREKERERARRDDAAAAAQ 20: Peptide 20:
                                   (SEQ ID NO: 50)
RDDAAAAAQKKKADAAKKSA 21: Peptide 21:
                                   (SEQ ID NO: 51)
KADAAKKSAAPAAKSAAPAA 22: Peptide 22:
                                   (SEQ ID NO: 52)
AAKSAAPAAKAAAPATKAAA 23: Peptide 23:
                                   (SEQ ID NO: 53)
AAPATKAAAAAPATKGAAPV 24: Peptide 24:
                                   (SEQ ID NO: 54)
PATKGAAPVKKSKK
```

Whole recombinant *Leishmania major* L19 (Lm L19) protein (i.e. SEQ ID NO:1) expressed in *Escherichia coli* was used as control Results Spleen Cells from naïve BALB/c mice ($5\times10^6$ cells/ml) were stimulated (final volume 200 ul) with each individual peptide (100 ug/ml), with a mixture of the 24 peptides (100 ug/ml), with the recombinant *Leishmania major* protein obtained from bacteria (12 ug/ml), and non-stimulated. After 48 h and 72 h supernatants were collected and the amount of IL-10 was measured by ELISA as earlier described herein.

The recombinant LmL19 obtained in bacteria was able to induce IL-10 synthesis in spleen cells from naive mice. None of the peptides were able to induce the same amount of IL-10 induced by the protein, However, statistically significant amounts of Il-10 were induced by peptides 1, 2, 12, 13, 14, 23 and 24.

Level of induced IL-10 was higher 72 h after stimulation in all cases.

Current Experiments with Peptides

We are repeating the experiments with new synthesized peptides in order to confirm the results obtained. According to these results, we are using the same peptides but we have included 3 new peptides containing the sequences of the peptides which induce the highest Il-10 levels. The composition of these peptides are:

```
25: Peptide 1-2:
                                   (SEQ ID NO: 55)
MTPLSLSSSRHSFKQNETQNMVSLKLQARLA 26: Peptide 12-13-14:
                                   (SEQ ID NO: 56)
LRRLLRKYRADKKIDRHVYRDLYMRAKGNYFRNKRNLVEHIH 27: Peptide: 23-24:
                                   (SEQ ID NO: 57)
AAPATKAAAAAPATKGAAPVKKSKK
```

Example 4: Animal Model for the Study of the
Anti-Inflammatory Effect of L19

Objective

The objectives of this study are: to test the anti-inflammatory effect of our active substance derived from Lm L19 (i.e. SEQ ID NO:1) expressed in *E. Coli* and tested in ex vivo cultures of intestinal tissue and; to investigate the anti-inflammatory effect in an animal model of Crohn's disease.

Methodology

To perform these objectives, two different steps will be taken:

1. In vitro assays with mucosal explants from patients of Crohns disease, healthy controls and healthy samples where inflammation has been induced in vitro with PMA-ionomycine. After 6 hours of incubation of samples with the active substance, supernatants will be analysed for presence of Pro-inflammatory cytokines, regulatory cytokines and chemokines such as TNFα, IL-10, etc.

RNA will be extracted from the different tissues in order to analyse the expression of genes coding for Cytokines, Chemokines, Transcription factors and Inflammatory signals.

Tissues will be digested to obtain mucosal mononuclear cells, where the expression of some cell markers will be studied in order to study the different states of the dendritic cells after incubation. The lymphocyte population will be also investigated in order to determine the specificity of the response to the active substance.

2. In vivo study of the anti-inflammatory effect of the active substance using murine inflammatory models in which chronic colitis is induced in the animals by the intake of drinking water with dextran sodium sulphate (DSS) for several days. Active substance will be inoculated subcutaneously in the animals before and after treatment with DSS. Different parameters such as quantitative evaluation of intestinal inflammation will be measured to evaluate the intestinal lesion (14) to (25).

REFERENCES

1. Zhou, X., et al, Current Drug Targets—Immune, Endocrine & Metabolic Disorders. 5(4), 2005, 465-475
2. Toshiyuki Y., et al, European Journal of Pharmacology. 533, 2006, 289-301
3. Weiss E., et al, Journal of the American Academy of Dermatology, 50(5), 2004, 657-675
4. Wan-Wan L., et al, The Journal of Clinical Investigation 117(5), 2007, 1175-83.
5. Wooley, Curr. Opin. Rheum. 3:407-20, 1999.
6. van Riel P. L. C. M., (2001), Best Practice & Research Clinical Rheumatology, 15: 67-76.
7. Gester A. M., (1999), Baillière's Clinical Immunology, 13: 629-644.
8. Neurath et al. Intern. Rev. Immunol. 19:51-62, 2000.
9. Ann Rheum Dis 2005; 64 (Suppl II):ii65-ii68. doi: 10.1136/ard. 2004.031237)
10. Hongbo Y., et al, Journal of Investigative Dermatology (2005) 125, 659-664.
11. Kirby B., et al, Br J Dermatol 2000; 142:728-32.
12. Remington: The Science and Practice of Pharmacy, 20th Edition. Baltimore, Md.: Lippincott Williams & Wilkins, 2000).
13. Zhou X. Et al, (2005), Curr. Drug Targets Immune Endocr. Metabol. Disord., 5(4): 465-475.
14. Sartor R. B., Gastroenterology 2008; 134(2):577-94.
15. Borruel N., et al, Gut 2002; 51: 659-664.
16. Borruel N., et al, Am J Gastroenterol 2003; 98: 865-870.
17. Carol M., et al, J Leukocyte Biol 2006; 79: 917-922.
18. Muñoz-Provencio D., et al, Arch Microbiol. 2008 Oct. 31.
19. Llopis M., et al, Inflamm Bowel Dis. 2009; 15: 275-283.
20. Lugea A., et al, Gut 2000; 46: 515-521.
21. Videla S., et al, Am J Gastroenterol 2001; 96: 1486-1493.
22. Medina C., et al, Scand J Gastroenterol 2001; 36: 1314-1319.
23. Medina C., et al, Am J Physiol 2003; 284: G116-G122.
24. Videla S., et al, J Pharmacol Exp Ther. 2006; 316: 940-945.
25. Videla S., et al, Dig Dis Sci 2007; 52: 45-51.

The invention claimed is:

1. A method for alleviating one or more symptom(s) and/or characteristic(s) and/or for improving a parameter of an inflammatory disorder in an individual in need thereof, the method comprising administering to said individual a nucleic acid molecule or a composition comprising at least said nucleic acid molecule in an amount effective to induce a detectable production of IL-10 or to induce a decrease of the production of IFNγ and/or TNFα, wherein said nucleic acid molecule is represented by a nucleotide sequence selected from the group consisting of:

(i) nucleotide sequences encoding a polypeptide comprising an amino acid sequence that has at least 78% sequence identity with the amino acid sequence of SEQ ID NO: 1, and (ii) nucleotide sequences comprising a nucleotide sequence that has at least 78% sequence identity with the nucleotide sequence of SEQ ID NO: 2.

2. The method of claim 1, wherein said nucleic acid molecule originates from *Leishmania major, Leishmania braziliensis, Leishmania infantum, Leishmania mexicana* or *Leishmania donovani.*

3. The method of claim 1, wherein the nucleic acid molecule is an oligonucleotide comprising at least 8, 10, 15, 20, 25, 30, 35, 40, 45, 50, 55, 60, 65, 70, 75, 80, 85, 90, 95, 100 or more contiguous nucleotides of SEQ ID NO:2.

4. The method of claim 1, wherein the inflammatory disorder is rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, and non-alcoholic steatosis, sarcoidosis, autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), cancer, systemic lupus erythematosus (SLE), sarcoidosis, and atopic dermatitis.

5. The method of claim 1, wherein the method comprises administering to said individual a pharmaceutical composition comprising at least said nucleic acid and a pharmaceutically acceptable carrier, adjuvant, salt, diluent and/or excipient.

6. A method for alleviating one or more symptom(s) and/or characteristic(s) and/or for improving a parameter of an inflammatory disorder in an individual in need thereof, the method comprising administering to said individual a polypeptide or a composition comprising said polypeptide in an amount effective to induce a detectable production of IL-10 or to induce a decrease of the production of IFNγ and/or TNFα, wherein said polypeptide is encoded by a nucleic acid which is represented by a nucleotide sequence selected from the group consisting of:
  (i) nucleotide sequences encoding a polypeptide comprising an amino acid sequence that has at least 78% sequence identity with the amino acid sequence of SEQ ID NO: 1, and
  (ii) nucleotide sequences comprising a nucleotide sequence that has at least 78% sequence identity with the nucleotide sequence of SEQ ID NO: 2.

7. The method of claim 6, wherein the nucleic acid molecule originates from *Leishmania major*, *Leishmania braziliensis*, *Leishmania infantum*, *Leishmania mexicana* or *Leishmania donovani*.

8. The method of claim 6, wherein the nucleic acid molecule is an oligonucleotide comprising at least 8, 10, 15, 20, 25, 30, 35, 40, 45, 50, 55, 60, 65, 70, 75, 80, 85, 90, 95, 100 or more contiguous nucleotides of SEQ ID NO: 2.

9. The method according to claim 6, wherein the inflammatory disorder is rheumatoid arthritis (RA), juvenile rheumatoid arthritis, psoriasis, psoriatic arthritis, ankylosing spondylitis, inflammatory bowel disease including Crohn's disease or ulcerative colitis, hepatitis, sepsis, alcoholic liver disease, and non-alcoholic steatosis autoimmune diabetes, diabetes mellitus, uveitis, multiple sclerosis, Controlling Allograft Rejection after organ transplantation, graft versus host disease (GVHD), inflammatory lung diseases including asthma and chronic obstructive pulmonary disease (COPD), cancer, systemic lupus erythematosus (SLE), sarcoidosis, and atopic dermatitis.

10. The method of claim 6, wherein the method comprises administering to said individual a pharmaceutical composition comprising said polypeptide and a pharmaceutically acceptable carrier, adjuvant, salt, diluent and/or excipient.

11. The method of claim 6, wherein the polypeptide is a protein fragment comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 210, 220, 230, 240, 250, 260, 265, or 267 contiguous amino acids of SEQ ID NO: 1.

12. The method of claim 11, wherein the protein fragment comprises at least 14 contiguous amino acids of SEQ ID NO: 1 and comprises SEQ ID NO: 31, 32, 55, 42, 43, 44, 56, 53, 54 and/or 57.

\* \* \* \* \*